United States Patent
Ägreda Navajas et al.

(10) Patent No.: US 10,857,136 B2
(45) Date of Patent: Dec. 8, 2020

(54) COMPOUNDS FOR USE IN THE PREVENTION AND/OR TREATMENT OF NON-ALCOHOLIC FAT LIVER DISEASE AND NON-ALCOHOLIC STEATOHEPATITIS

(71) Applicant: SJT MOLECULAR RESEARCH, SL, Álava (ES)

(72) Inventors: Juan Carlos Ägreda Navajas, Vitoria (ES); Roberto Mikio Kassuya, Vitoria (ES)

(73) Assignee: SJT MOLECULAR RESEARCH, SL, Álava (ES)

( * ) Notice: Subject to any disclaimer, the term of this patent is extended or adjusted under 35 U.S.C. 154(b) by 0 days.

(21) Appl. No.: 16/490,670

(22) PCT Filed: Feb. 19, 2018

(86) PCT No.: PCT/EP2018/053990
§ 371 (c)(1),
(2) Date: Sep. 3, 2019

(87) PCT Pub. No.: WO2018/166756
PCT Pub. Date: Sep. 20, 2018

(65) Prior Publication Data
US 2020/0016129 A1    Jan. 16, 2020

Related U.S. Application Data

(60) Provisional application No. 62/471,105, filed on Mar. 14, 2017.

(51) Int. Cl.
| | | |
|---|---|---|
| *A61K 31/437* | (2006.01) | |
| *A61P 1/16* | (2006.01) | |
| *A61K 31/496* | (2006.01) | |
| *A61K 31/5377* | (2006.01) | |

(52) U.S. Cl.
CPC .......... *A61K 31/437* (2013.01); *A61K 31/496* (2013.01); *A61K 31/5377* (2013.01); *A61P 1/16* (2018.01)

(58) Field of Classification Search
CPC .................................................... A61K 31/437
See application file for complete search history.

(56) References Cited

U.S. PATENT DOCUMENTS

| | | |
|---|---|---|
| 2010/0233133 A1 | 9/2010 | Leek |
| 2011/0092510 A1 | 4/2011 | Klein et al. |
| 2015/0342943 A1 | 3/2015 | Bornstein et al. |
| 2016/0340355 A1 | 11/2016 | Agreda Navajas et al. |

FOREIGN PATENT DOCUMENTS

| | | |
|---|---|---|
| WO | 2004/093871 A1 | 11/2004 |
| WO | 2009/147125 A1 | 12/2009 |
| WO | 2012/130912 A1 | 10/2012 |
| WO | 2015/187499 A1 | 12/2015 |

OTHER PUBLICATIONS

Petta S, et a.; "Non-alcoholic fatty liver disease pathogenesis: the present and the future," Digestive and Liver Disease, 2009; 41(9):615-25.
Neuschwander-Tetri Ba; "Non-alcoholic fatty liver disease," BMC Medicine 2017;15(1):45. DOI 10.1186/s12916-017-0806-8.
Bellentani S.; "The epidemiology of non-alcoholic fatty liver disease," Liver International; 2017;37 Suppl 1:81-84; DOI: 10.1111. liv.13299.
Hameed B. et al.; "Emerging Therapies for Nonalcoholic Fatty Liver Disease," Clin Liver Dis. 2015; 20(2):365-85. http://dx.doi.org/10.1016/j.cld.2015.10.015.
Bashiardes S, et al.; "Non-alcoholic fatty liver and the gut microbiota," Molecular Metabolism. 2016; 5(9):782-94; http://dx/doi.org.10.1016/j.molmet.2016.06.003.
Barb D.; "Pharmacological management of nonalcoholic fatty liver disease," Metabolism Clinical and Experimental, 2016; 65(8):1183-95.

(Continued)

*Primary Examiner* — Golam M Shameem
(74) *Attorney, Agent, or Firm* — Tristan A. Fuierer; Olive Law Group, PLLC

(57) ABSTRACT

Compounds of formula I,

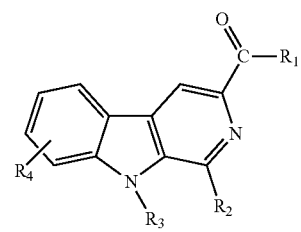

and their pharmaceutical and food grade acceptable salts, for use in the prevention and/or treatment of NAFLD (non-alcoholic fat liver disease) or NASH (non-alcoholic steatohepatitis), and related symptoms and/or associated pathologies thereof are described. Also described are pharmaceutical compositions or nutraceutical compositions comprising said compounds of formula I, and their pharmaceutically, or food grade, acceptable or allowable, salts and combinations thereof, optionally with any inert ingredient, carrier, excipient or alike for use in the prevention and/or treatment of NAFLD or NASH, and related symptoms and/or associated pathologies thereof. Additionally described are methods for the prevention and/or treatment of NAFLD or NASH, and related symptoms and/or associated pathologies thereof comprising the administration to a subject in need thereof, of any compound of formula I, and pharmaceutical and food grade acceptable salts thereof, or any pharmaceutical compositions, functional food additives or nutraceutical compositions comprising the same.

19 Claims, 20 Drawing Sheets

(56) References Cited

OTHER PUBLICATIONS

Ratziu V.; "Novel Pharmacotherapy Options for NASH," Dig Dis Sci. 2016; 61(5):1398-405. DOI 10.1007/s10620-016-4128-z.
Rotman Y; "Current and upcoming pharmacotherapy for non-alcoholic fatty liver disease," Gut 2017; 66(1):180-190; doi:10.1136/gutjnl-2016-312431.
Zhiyoing Chen, et al, "Synthesis, cytotoxic activities and DNA binding properties of beta-carboline derivatives," European Journal of Medicinal Chemistry. 45 (2010) 4740-4745.
Ying Li et al.; "Beta-carboline derivatives and diphenols from soy sauce are in vitro quinone reductase (QR) inducers," Journal of Agricultural Food Chemistry, 2001, 59, 2332-2340.
International Search Report, dated May 24, 2018.

FIGURE 2A
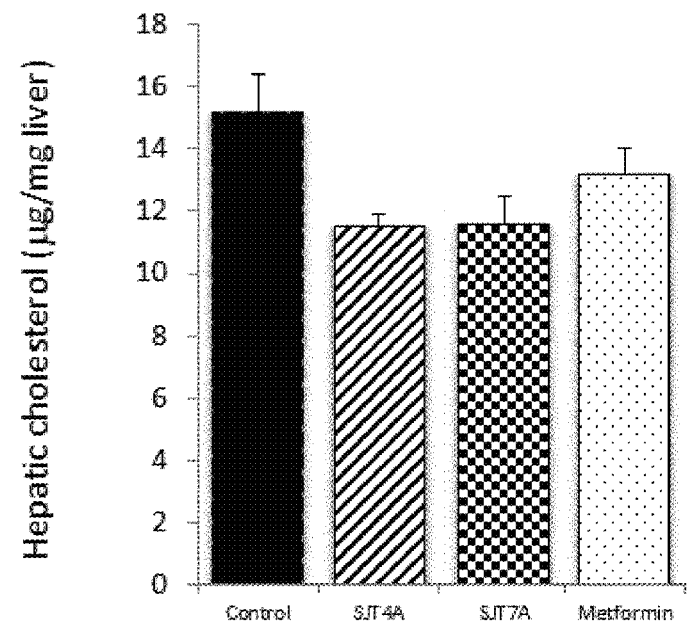
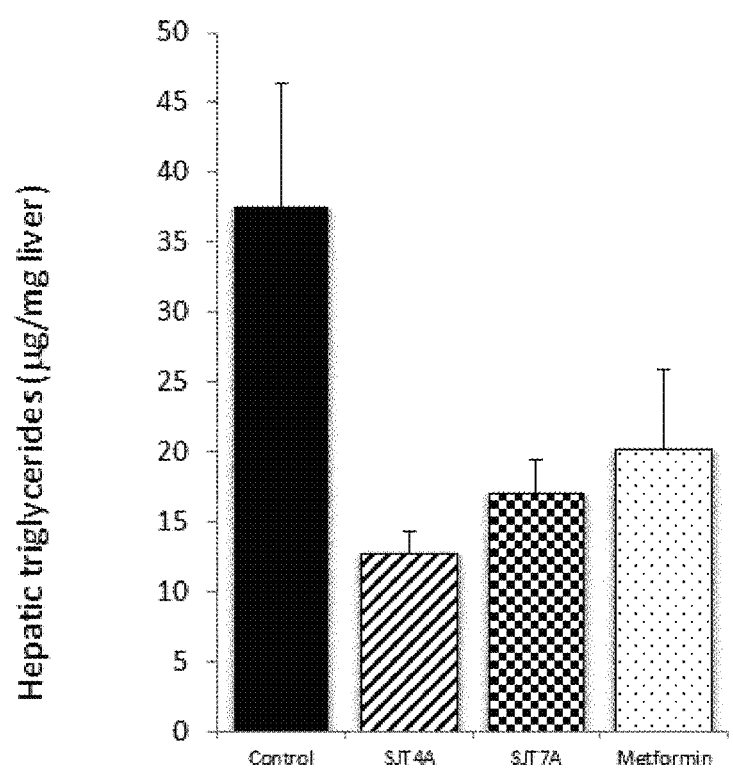
FIGURE 2B

LEAN-CHOW Vehicle
NAS

A

DIO-NASH Vehicle
NAS

B

SJT4a
NAS

C

CHOW-LEAN Vehicle

DIO-NASH Vehicle

SJT4a

CHOW-LEAN Vehicle

DIO-NASH Vehicle

SJT4a

COMPOUNDS FOR USE IN THE PREVENTION AND/OR TREATMENT OF NON-ALCOHOLIC FAT LIVER DISEASE AND NON-ALCOHOLIC STEATOHEPATITIS

CROSS-REFERENCE TO RELATED APPLICATIONS

This application is filed under the provisions of 35 U.S.C. § 371 and claims the priority of International Patent Application No. PCT/EP2018/053990, filed on 19 Feb. 2018 entitled "COMPOUNDS FOR USE IN THE PREVENTION AND/OR TREATMENT OF NON-ALCOHOLIC FAT LIVER DISEASE AND NON-ALCOHOLIC STEATOHEPATITIS" in the name of Elier PAZ ROJAS, et al., which claims priority to U.S. Provisional Patent Application No. 62/471,105 filed on 14 Mar. 2017, both of which are hereby incorporated by reference herein in their entirety.

FIELD OF THE INVENTION

Present invention refers a family of compounds for use in the prevention and/or treatment of non-alcoholic fatty liver disease (NAFLD) and non-alcoholic steatohepatitis (NASH), as well as in the prevention and/or treatment of all related manifestation or symptoms of those liver disorders.

INVENTION BACKGROUND

Non-alcoholic fatty liver disease (NAFLD) and its severe evolved stage, non-alcoholic steatohepatitis (NASH), are emerging therapeutic areas. NAFLD is characterized by the abnormal accumulation of fat in the liver as lipid droplets within the liver parenchyma, affecting individuals with a non-significant alcohol consumption (1, 2). It is the most frequent liver disorder worldwide, affecting to 6-35% of general population, being one of the major causes of liver transplantation after progressing to cirrhosis and hepatocellular carcinoma (3).

The exact cause of NAFLD is still unknown. However, among other diseases, insulin resistance is considered to play a role in the disease process. The exact reasons and mechanisms by which the disease progresses from one stage to the next are not completely understood.

The evolution of the disease has been explained by a "two-hit hypothesis", the first hit represented by lipid accumulation in the hepatocytes, followed by a second hit by which oxidative stress and inflammation lead to NASH (1). The initial metabolic stress generated by lipid accumulation in the hepatocytes trigger multiple cell stress pathways, including endoplasmic reticulum stress, mitochondrial dysfunction, oxidative stress (generation of reactive oxygen species), apoptosis and even necrosis. The generated hepatocellular injury leads to the release of signals that recruit and activate a variety of immune cells producing an inflammatory response. Those events converge to activate hepatic stellate cells inducing an increase of collagen deposition resulting in fibrosis and may eventually progress to cirrhosis and hepatocellular carcinoma (4). Other external inputs, from behavioural habits (diet/lifestyle/physical exercise) to microbiota components can contribute to disease development (5).

Up to date, many therapeutic strategies have been proposed and a number of candidate agents have been tested. However, none of them have been still approved for the treatment of NASH (6-8). Different targets and strategies have been explored in the search for an efficient therapy to treat NAFDL and NASH. They include:

Insulin sensitizers: PPAR agonists, incretins analogues (GLP-1 receptor agonists), DPP-4 inhibitors, SGLT2 inhibitors, ACE inhibitors and angiotensin-II receptor blockers (anti-hypertensive agents).

Bile acid regulators: farnesoid X-receptor agonists (negatively regulate bile acid synthesis and decrease hepatic lipogenesis and steatosis)

Inhibitors of de novo lipogenesis: stearoyl CoA desaturase and acetyl-CoA carboxylase inhibitors Lipid-lowering agents: statins, fibrates, lipase inhibitors Antioxidants: vitamin E, cysteamine Anti-inflammatory agents: TNF-α inhibitors Immune modulators: $I_κB$ inhibitors, inflammatory chemokines antagonists (CCR2/CCR5 inhibitors), VAP1 inhibitors Anti-apoptotic agent: caspase inhibitors, ASK1 inhibitors Gut microbiome modulators: antibiotics, anti-LPS IgG-rich extracts, faecal microbiota transplantation Antifibrotics: galectin-3 inhibitors, LOXL2 blockers Although galectin-3 is considered a target for fibrosis, it is also a marker for liver inflammation, as measured in the examples included in present disclosure. Since, as mentioned above, none of those approaches have still resulted in compounds approved for the treatment of NASH, there is a clear need to develop alternatives to those approaches to treat and prevent said disease.

DESCRIPTION

Present invention provides compounds for use in methods to lower the liver fat content associated to non-alcoholic hepatic steatosis or steatohepatitis. In particular, it is the problem of present disclosure to provide compounds and methods for the prevention and/or treatment of non-alcoholic fatty liver disease (NAFLD) and its severe evolved stage, non-alcoholic steatohepatitis (NASH).

NAFLD is considered to cover a spectrum of disease activity. This spectrum begins, as explained, with fat accumulation in the liver (hepatic steatosis). Although the liver can remain fatty without disturbing liver function, different mechanisms and possible aggressions to the liver may progress and result in the development of non-alcoholic steatohepatitis (NASH), a state in which steatosis is combined with inflammation and fibrosis (steatohepatitis).

Therefore, this disease progression from NAFLD to NASH involves different symptoms and/or associated pathologies which are directly connected to said disorders.

For the early stages said symptoms and/or associated pathologies refer to insulin resistance and lipid accumulation in the hepatocytes which triggers multiple cell stress pathways, including endoplasmic reticulum stress, mitochondrial dysfunction, oxidative stress (generation of reactive oxygen species), apoptosis and even necrosis.

In a second stage, the generated hepatocellular injury leads to symptoms of NAFLD related to inflammation.

Those events converge to activate hepatic stellate cells inducing an increase of collagen deposition resulting in increased fibrosis, cirrhosis and hepatocellular carcinoma as associated pathologies of those disorders.

It is thus the problem solved by present invention to provide compounds of formula I for use in the prevention and/or treatment of the symptoms and/or associated pathologies of NAFLD and of NASH in all the stages of their development; preferably wherein the related symptoms are independently selected from insulin resistance, lipid accumulation in the hepatocytes, mitochondrial dysfunction, oxidative stress, apoptosis, necrosis, inflammation or fibrosis; and preferably wherein the associated pathologies are cirrhosis or hepatocellular carcinoma.

The compounds of formula I disclosed in present invention, and synthesis thereof, were disclosed in the international patent application PCT/EP2012/055570, filed on Mar. 28 2012. According to PCT/EP2012/055570 said compounds are useful in the treatment of metabolic syndrome. The applicant has now surprisingly found that said compounds, and intermediates of synthesis thereof, are also useful in the prevention and/or treatment of NAFLD or NASH, and also in the prevention and/or treatment of related manifestations or symptoms thereof.

Therefore, present invention relates to a compound of general formula I and any pharmaceutically or food grade acceptable salt thereof:

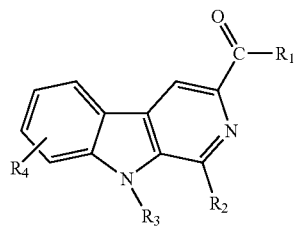

(I)

wherein, independently,
$R_1$ can selected from: linear or cycled mono or dialkylamines; $OR_9$, aminoalkylalcohols or aminoalkylethers;
$R_2$ can be selected from: benzene or heterocycle rings;
$R_3$ can be selected from: H; a hydrocarbon radical selected from straight or branched alkyl of from 1 to 5 carbons; or benzyl group;
$R_4$ can be selected from: H; a hydrocarbon radical selected from straight or branched alkyl of from 1 to 5 carbons; hydroxy or alkoxy radicals; or halogen; and
$R_9$ is an alkyl group;
for use in the treatment of non-alcoholic fat liver disease (NAFLD) and non-alcoholic steatohepatitis (NASH), and/or related symptoms and/or related pathologies thereof.

An embodiment relates to a compound of formula I, as disclosed herein, for use in the treatment of non-alcoholic fat liver disease (NAFLD) and non-alcoholic steatohepatitis (NASH), and/or related symptoms and/or related pathologies thereof, wherein the related symptoms are independently selected from insulin resistance, lipid accumulation in the hepatocytes, mitochondrial dysfunction, oxidative stress, apoptosis, necrosis, inflammation or fibrosis; and wherein the associated pathologies are cirrhosis or hepatocellular carcinoma.

Preferred compounds of general formula I for use, according to present invention, are those that, independently,
$R_1$ when being a linear alkylamine is selected from: NH—$(CH_2)_n$—$NH_2$, NH—$(CH_2)_n$—$N(CH_3)_2$;
being n a value between 0 and 4; NH—N=CH-phenyl-$R_7$;
and $R_1$ when being a cycled amine is selected from:

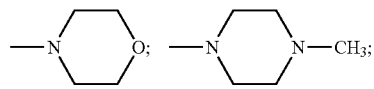

$R_1$ when being an aminoalkylalcohol group is $HNCH_2CH_2OH$; and when being an aminoalkylether group is $HNCH_2CH_2OCH_3$;
$R_1$ when being $OR_9$, $R_9$ is a $C_{1-4}$ alkyl group;
$R_2$, when being a benzene substituted ring is selected from:

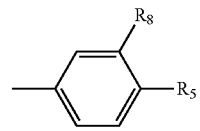

and when being a heterocycle ring is

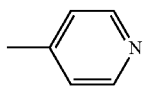

$R_3$ when being a hydrocarbon radical selected from straight alkyl of from 1 to 5 carbons, is methyl;
$R_4$ when being a hydrocarbon radical selected from straight alkyl of from 1 to 5 carbons, is methyl; $R_4$ when being an alkoxy radical is a radical methoxy;
and $R_4$ when being a halogen is fluorine;
$R_5$ can be selected from: H; alkoxy; halogen; hydroxy; or halogen-alkyl;
$R_7$ can be selected from: H or $NO_2$;
$R_8$ can be selected from: H; hydroxy; alkoxy.

The term "pharmaceutically acceptable salt" refers to any salt, which upon administration to the patient is capable of providing (directly or indirectly) a compound as described herein.

The term "food grade acceptable salt" refers to any salt of the products described which can be administered in any functional food additive or nutraceutical composition.

Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

In a preferred embodiment of the invention, the salt is a hydrochloride salt.

Therefore, present invention refers to the compounds of formula I and any pharmaceutically or food grade acceptable salt thereof, described above herein, for use in the prevention and/or treatment of NAFLD or NASH, and related symptoms and/or associated pathologies thereof.

Present invention also refers to the use of the compounds of formula I and any pharmaceutically or food grade acceptable salt thereof, for the manufacture of a medicament for the prevention and/or treatment of NAFLD or NASH, and related symptoms and/or associated pathologies thereof.

Additionally, present invention refers to a method of preventing and/or treating a subject suffering from NAFLD or NASH, or suffering from any related symptoms and/or associated pathologies thereof, comprising administering to said subject an effective quantity of the compounds of formula I and any pharmaceutically or food grade acceptable salt thereof, disclosed herein.

Preferred compounds for use in the prevention and/or treatment of NAFLD or NASH, and related symptoms and/or associated pathologies thereof, described in present invention are compounds of formula I wherein, $R_5$ can be selected from: H, methoxy; chlorine, OH or trifluoromethyl, preferably, when $R_5$ is H, $R_8$ is OH and when $R_5$ is OH, $R_8$ is H or $OCH_3$.

Preferred compounds for use according to present invention are compounds of formula I wherein $R_9$ is methyl.

Preferred compounds for use according to present invention are compounds of formula I, wherein, $R_2$ is

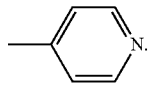

Preferred compounds for use according to present invention are compounds of formula I wherein $R_3$ is methyl or benzyl.

Preferred compounds for use according to present invention are compounds of formula I wherein $R_4$ is methyl, methoxy or fluorine.

Preferred compounds according to present disclosure are compound of formula I

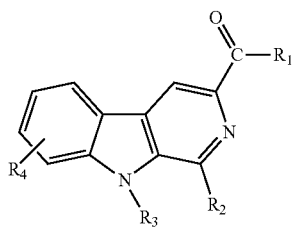

wherein:
$R_1$ is selected from $OR_9$; $NH-(CH_2)_n-NH_2$, $NH-(CH_2)_n-N(CH_3)_2$; being n a value between 0 and 4; $HNCH_2CH_2OH$; $HNCH_2CH_2OCH_3$; $NH-N=CH$-phenyl-$R_7$; or a cycled amine
$R_2$ is selected from

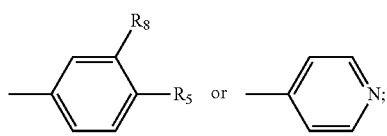

$R_3$ can be selected from: H; a hydrocarbon radical selected from straight or branched alkyl of from 1 to 5 carbons; or benzyl group;
$R_4$ can be selected from: H; a hydrocarbon radical selected from straight or branched alkyl of from 1 to 5 carbons; hydroxy or alkoxy radicals; or halogen; and
$R_7$ is H or p-$NO_2$
$R_5$ is selected from: H; alkoxy; halogen; hydroxy; or halogen-alkyl;

$R_8$ is selected from: H; hydroxy; alkoxy;
$R_9$ is methyl;
or a pharmaceutically acceptable salt thereof;
for use in the prevention and/or treatment of NAFLD or NASH, and related symptoms and/or associated pathologies thereof.

Additionally, preferred compounds according to present disclosure are compounds of formula I

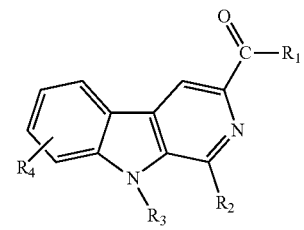

wherein:
$R_1$ is selected from $NH-(CH_2)_n-NH_2$, $NH-(CH_2)_n-N(CH_3)_2$; being n a value between 0 and 4; $HNCH_2CH_2OH$; $HNCH_2CH_2OCH_3$; $NH-N=CH$-phenyl-$R_7$; or a cycled amine selected from:

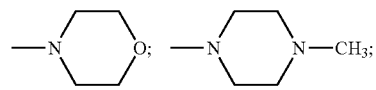

$R_2$ is selected from

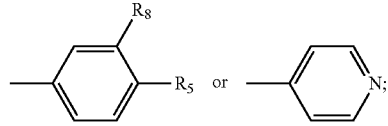

$R_3$ is selected from H, methyl or benzyl;
$R_4$ is selected from H, methyl, methoxy or fluorine;
$R_7$ is H or p-$NO_2$
$R_8$ is H, OH or methoxy; and
$R_5$ is H, OH or methoxy;
or a pharmaceutically acceptable salt thereof;
for use in the prevention and/or treatment of NAFLD or NASH, and related symptoms and/or associated pathologies thereof.

In a preferred embodiment, the pharmaceutically acceptable salt is a hydrochloride salt.

Additionally, preferred compounds for use according to present invention are the ones having formula II or III Formula II

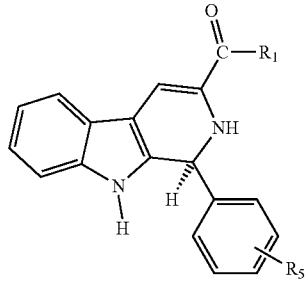

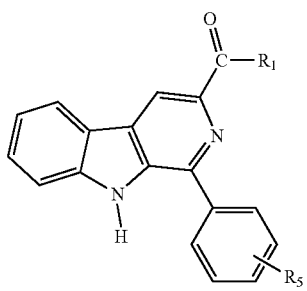

Formula III wherein, independently, $R_1$ can selected from: OH, $OCH_3$, NH—$(CH_2)_n$—$N(CH_3)_2$, NH—$(CH_2)_n$—$NH_2$ being n a value between 0 and 3; NH—$(CH_2)_2$—OH; NH—$(CH_2)_2$—$OCH_3$ or NH—N=CH-phenyl-$R_7$;

$R_5$ can be selected from: $OCH_3$ or H;

$R_7$ can be selected from: H or p-$NO_2$

More particularly, preferred compounds for use according to present invention are those wherein, when $R_1$ is a group OH, $R_5$ is selected from H or p-$OCH_3$.

Still preferred compounds for use according to present invention are those having a formula II selected from formula 1a, wherein $R_1$ is a group OH, and $R_5$ is p-$OCH_3$; or from formula 1b, wherein $R_1$ is a group OH and $R_5$ is H.

Also, preferred compounds for use according to present invention are those wherein, when $R_1$ is a group $OCH_3$, $R_5$ is selected from H or p-$OCH_3$.

Preferred compounds for use according to present invention are those having a formula II selected from: formula 2a, wherein $R_1$ is a group $OCH_3$ and $R_5$ is p-$OCH_3$; from formula 2b, wherein $R_1$ is a group $OCH_3$ and $R_5$ is H; or having a formula III selected from formula 3a, wherein $R_1$ is a group $OCH_3$ and $R_5$ is p-$OCH_3$ or from formula 3b, wherein $R_1$ is a group $OCH_3$, and $R_5$ is H.

Also, preferred compounds for use according to present invention are those wherein, when $R_1$ is a group NH—$(CH_2)_n$—$NH_2$, being the value of n=2 or 3, $R_5$ is p-$OCH_3$.

Preferred compounds for use according to present invention are those having a formula III selected from formula 4a, wherein $R_1$ is $NH(CH_2)_2NH_2$ and $R_5$ is p-$OCH_3$; or from formula 5a, wherein $R_1$ is $NH(CH_2)_3NH_2$ and $R_5$ is p-$OCH_3$.

A more preferred compound for use according to present invention is 4a wherein when $R_1$ is a group NH—$(CH_2)_n$—$NH_2$, being the value of n=2, $R_5$ is p-$OCH_3$.

A more preferred compound for use according to present invention is 5a wherein when $R_1$ is a group NH—$(CH_2)_n$—$NH_2$, being the value of n=3, $R_5$ is p-$OCH_3$.

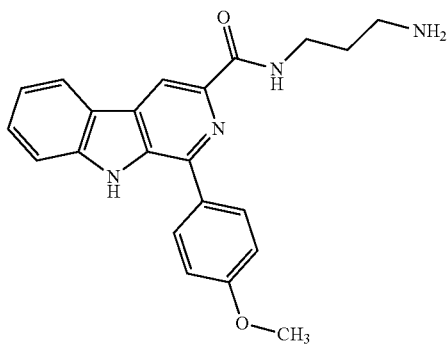

5a

More preferred compounds for use according to the present invention are the ones having formula III, wherein, when $R_1$ is a group NH—$(CH_2)_n$—$NH_2$, being the value of n=0, $R_5$ is selected from H or p-$OCH_3$.

Within the compounds for use according to present invention are also comprised those having a formula III selected from formula 6a, wherein $R_1$ is $NHNH_2$ and $R_5$ is p-$OCH_3$; or from formula 6b, wherein $R_1$ is $NHNH_2$ and $R_5$ is H.

More particularly, preferred compounds for use according to present invention are those wherein, in formula III, when being $R_1$ a group NH—N=CH-phenyl, $R_5$ is p-$OCH_3$ and when being $R_1$ a group NH—N=CH-phenyl substituted by a group p-$NO_2$, $R_5$ is H.

Within the compounds for use according to present invention are also included the ones having a formula III selected from formula 7a, wherein $R_1$ is a group NH—N=CH-phenyl and $R_5$ is p-$OCH_3$; or from formula 7b, wherein $R_1$ is a group NH—N=CH-phenyl-p-$NO_2$ and $R_5$ is H.

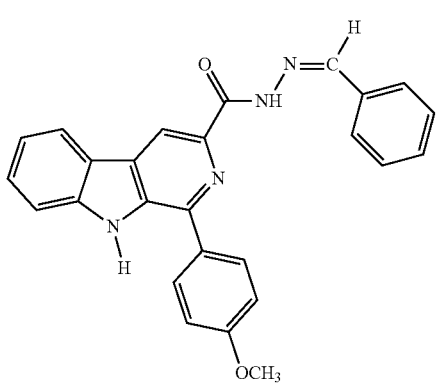

7a

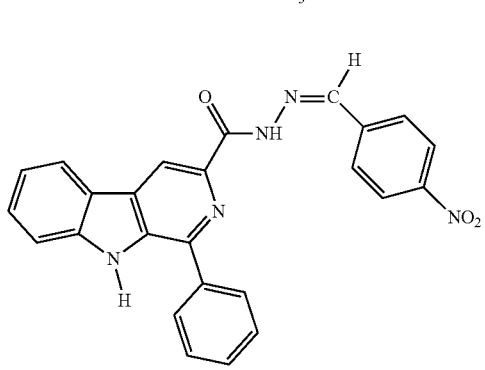

7b

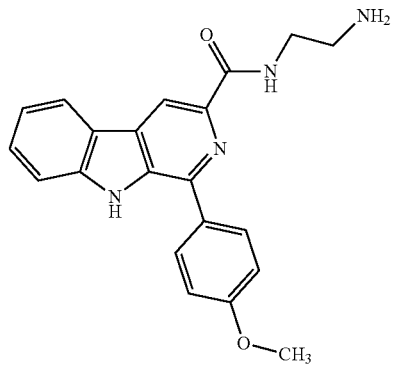

4a

Also, preferred compounds for use according to present invention are those having a formula III wherein, when $R_1$ is a group $NH—(CH_2)_n—N(CH_3)_2$, being the value of n=2, $R_5$ is p-OCH$_3$.

Also, preferred compounds for use according to present invention are those having a formula III wherein, when $R_1$ is a cycled amine selected from

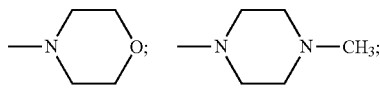

and
$R_5$ is p-OCH$_3$.

Also, preferred compounds for use according to present invention are those having a formula III wherein, when $R_1$ is $NH—(CH_2)_n—N(CH_3)_2$, being the value of n=4 and $R_5$ is p-OCH$_3$.

Also, preferred compounds for use according to present invention are those having a formula III wherein, when $R_1$ is $NH—(CH_2)_2—OH$ and $R_5$ is p-OCH$_3$.

Also, preferred compounds for use according to present invention are those having a formula III wherein, when $R_1$ is $NH—(CH_2)_2—OCH_3$ and $R_5$ is p-OCH$_3$.

Also, preferred compounds for use according to present invention are those having a formula III wherein, when $R_1$ is $NH—(CH_2)_n—N(CH_3)_2$, being the value of n=2 and $R_5$ is chlorine.

Also, preferred compounds for use according to present invention are those having a formula III wherein, when $R_1$ is $NH—(CH_2)_n—N(CH_3)_2$, being the value of n=2 and $R_5$ is OH.

Also, preferred compounds for use according to present invention are those having a formula III wherein, when $R_1$ is $NH—(CH_2)_n—N(CH_3)_2$, being the value of n=2 and $R_5$ is trifluoromethyl.

A preferred embodiment refers to a compound of formula I, II or III, or a pharmaceutical salt thereof, or a pharmaceutical composition comprising an effective amount of said compound, for use in the prevention and/or treatment of non-alcoholic fat liver disease (NAFLD) and non-alcoholic steatohepatitis (NASH), and/or related symptoms and/or related pathologies thereof, wherein the related symptoms are independently selected from insulin resistance, lipid accumulation in the hepatocytes, mitochondrial dysfunction, oxidative stress, apoptosis, necrosis, inflammation or fibrosis; and wherein the associated pathologies are cirrhosis or hepatocellular carcinoma.

A preferred embodiment refers to a compound of formula I, II or III, or a pharmaceutical salt thereof, or a pharmaceutical composition comprising said compound, for use in the prevention and/or treatment of non-alcoholic fat liver disease (NAFLD).

A preferred embodiment refers to a compound of formula I, II or III, or a pharmaceutical salt thereof, or a pharmaceutical composition comprising said compound, for use in the prevention and/or treatment of non-alcoholic steatohepatitis (NASH).

A preferred embodiment refers to a compound of formula I, II or III, or a pharmaceutical salt thereof, or a pharmaceutical composition comprising said compound, for use in the prevention and/or treatment of insulin resistance, lipid accumulation in the hepatocytes, mitochondrial dysfunction, oxidative stress, apoptosis, necrosis, inflammation or fibrosis.

A preferred embodiment refers to a compound of formula I, II or III, or a pharmaceutical salt thereof, or a pharmaceutical composition comprising said compound, for use in the prevention and/or treatment of insulin resistance, liver lipid accumulation, liver inflammation or liver fibrosis.

A preferred embodiment refers to a compound of formula I, II or III, or a pharmaceutical salt thereof, or a pharmaceutical composition comprising said compound, for use the prevention and/or treatment of cirrhosis or hepatocellular carcinoma.

The invention also includes pharmaceutical compositions, functional food additives or nutraceutical compositions comprising at least any of the previously mentioned compounds represented by general formulas I, II and III, and their pharmaceutically, or food grade, acceptable or allowable, salts and combinations thereof, optionally with any inert ingredient, carrier, excipient or alike for use in the prevention and/or treatment of NAFLD or NASH, and related symptoms and/or associated pathologies thereof.

The invention also comprises any of the compounds covered by general formula I and any pharmaceutically salt thereof, as previously disclosed, or any pharmaceutical composition comprising the same, for use in the prevention and/or treatment of NAFLD or NASH, and related symptoms and/or associated pathologies thereof.

Additionally, present invention relates to a pharmaceutical composition comprising an effective amount of at least one compound of formula I, as described herein, for use in the prevention and/or treatment of non-alcoholic fat liver disease (NAFLD) and non-alcoholic steatohepatitis (NASH), and/or related symptoms and/or related pathologies thereof.

An effective amount, for the purposes of present invention is that which provides either subjective relief of symptoms or an objectively identifiable improvement as noted by the clinician or other qualified observer.

Present invention relates also to a pharmaceutical composition comprising an effective amount of at least one compound of formula I, or pharmaceutically acceptable salt thereof:

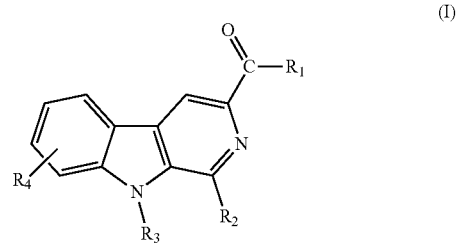

(I)

wherein, independently,
$R_1$ is selected from linear or cycled mono or dialkylamines; $OR_9$, aminoalkylalcohols or aminoalkylethers;
$R_2$ is selected from benzene or heterocycle rings;
$R_3$ is selected from H; a hydrocarbon radical selected from straight or branched alkyl of from 1 to 5 carbons; or a benzyl group;
$R_4$ is selected from H; a hydrocarbon radical selected from straight or branched alkyl of from 1 to 5 carbons; hydroxy or alkoxy radicals; or halogen; and
$R_9$ is an alkyl group;
and at least one pharmaceutically acceptable excipient, for use in the prevention and/or treatment of non-alcoholic fat liver disease (NAFLD) and non-alcoholic steatohepatitis (NASH), and/or related symptoms and/or related pathologies thereof.

Additionally disclosed is a pharmaceutical composition for use, as described above herein, comprising an effective amount of at least one compound of formula I, and at least one pharmaceutically acceptable excipient, wherein:

$R_1$ is selected from NH—$(CH_2)_n$—$NH_2$, NH—$(CH_2)_n$—$N(CH_3)_2$; being n a value between 0 and 4; $HNCH_2CH_2OH$; $HNCH_2CH_2OCH_3$; NH—N=CH-phenyl-$R_7$; or a cycled amine selected from:

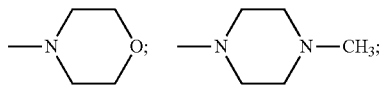

$R_2$ is selected from

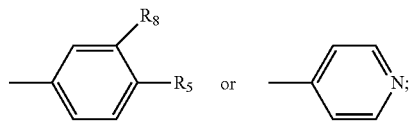

$R_3$ is selected from H, methyl or benzyl;
$R_4$ is selected from H, methyl, methoxy or fluorine;
$R_7$ is H or p-$NO_2$
$R_8$ is H, OH or methoxy; and
$R_5$ is H, OH or methoxy.

Additionally, the invention also comprises any of the compounds covered by general formula I, II or III and any pharmaceutically salt thereof, as previously disclosed, and a further second active compound, for use in the prevention and/or treatment of NAFLD or NASH, and related symptoms and/or associated pathologies thereof. Said second active compound can be administered simultaneously, sequentially or independently with any of the compounds covered by general formula I, II or III and any pharmaceutically salt thereof.

For the purposes of present invention, an "active compound or active principle" should be taken as synonyms and mean a chemical entity which exerts therapeutic effects when administered to human or animal beings. Said second active compound can be independently selected from insulin sensitizers, bile acid regulators, inhibitors of de novo lipogenesis, lipid-lowering agents, antioxidants, anti-inflammatory agents, immune modulators, anti-apoptotic agents, gut microbiome modulators, or antifibrotics.

For the purpose of present invention insulin sensitizers include but are not limited to PPAR agonists, incretins analogues (GLP-1 receptor agonists), DPP-4 inhibitors, SGLT2 inhibitors, ACE inhibitors or angiotensin-II receptor blockers (anti-hypertensive agents). Bile acid regulators include but are not limited to farnesoid X-receptor agonists. Inhibitors of de novo lipogenesis include but are not limited to stearoyl CoA desaturase or acetyl-CoA carboxylase inhibitors. Lipid-lowering agents include but are not limited to statins, fibrates or lipase inhibitors. Antioxidants include but are not limited to vitamin E or cysteamine. Anti-inflammatory agents include but are not limited to TNF-α inhibitors. Immune modulators include but are not limited to $I_KB$ inhibitors, inflammatory chemokines antagonists (CCR2/CCR5 inhibitors) or VAP1 inhibitors. Anti-apoptotic agents include but are not limited to caspase inhibitors or ASK1 inhibitors. Gut microbiome modulators include but are not limited to antibiotics, anti-LPS IgG-rich extracts or faecal microbiota transplantation. Antifibrotics include but are not limited to galectin-3 inhibitors or LOXL2 blockers.

Present invention relates also to the use of a nutraceutical composition comprising at least one compound of formula I, or food grade acceptable salt thereof:

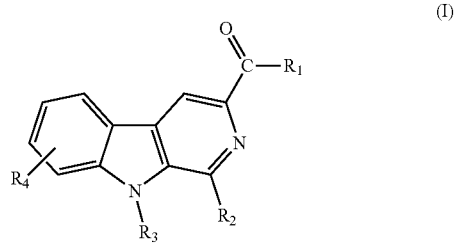

wherein, independently,
$R_1$ is selected from linear or cycled mono or dialkylamines; $OR_9$, aminoalkylalcohols or aminoalkylethers;
$R_2$ is selected from benzene or heterocycle rings;
$R_3$ is selected from H; a hydrocarbon radical selected from straight or branched alkyl of from 1 to 5 carbons; or a benzyl group;
$R_4$ is selected from H; a hydrocarbon radical selected from straight or branched alkyl of from 1 to 5 carbons; hydroxy or alkoxy radicals; or halogen; and
$R_9$ is an alkyl group;
and at least one food grade acceptable excipient, for alleviating and/or preventing non-alcoholic fat liver disease (NAFLD), non-alcoholic steatohepatitis (NASH), and/or related symptoms and/or related pathologies thereof.

Additionally disclosed is the use of a nutraceutical composition, as described above herein, comprising an effective amount of at least one compound of formula I, and at least one pharmaceutically acceptable excipient, wherein:

$R_1$ is selected from NH—$(CH_2)_n$—$NH_2$, NH—$(CH_2)_n$—$N(CH_3)_2$; being n a value between 0 and 4; $HNCH_2CH_2OH$; $HNCH_2CH_2OCH_3$; NH—N=CH-phenyl-$R_7$; or a cycled amine selected from:

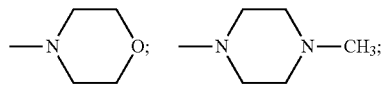

$R_2$ is selected from

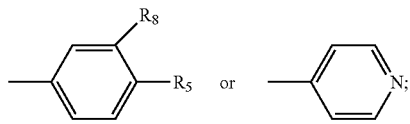

$R_3$ is selected from H, methyl or benzyl;
$R_4$ is selected from H, methyl, methoxy or fluorine;
$R_7$ is H or p-$NO_2$
$R_8$ is H, OH or methoxy; and
$R_5$ is H, OH or methoxy.

The invention comprises the use of any of the compounds covered by general formula I, II or III, and any pharmaceutically salt thereof, as previously disclosed, or pharmaceutical compositions comprising the same in the manufacture of a medicament for the prevention and/or treatment of NAFLD or NASH, and related symptoms and/or associated pathologies thereof.

The invention further comprises a method of preventing and/or treating a subject suffering from NAFLD or NASH, or suffering from any related symptoms and/or associated pathologies thereof, comprising administering to said subject an effective quantity of any of the compounds covered by general formula I, II or III, and any pharmaceutically or food grade acceptable salt thereof, or of pharmaceutical, food additive or nutraceutical compositions comprising the same.

The invention further comprises a method of preventing and/or treating a subject suffering from NAFLD or NASH, or suffering from any related symptoms and/or associated pathologies thereof, comprising administering to said subject a pharmaceutical composition comprising any of the compounds covered by general formula I, II or III, and any pharmaceutically acceptable salt thereof.

Additionally, the invention further comprises a method of preventing and/or treating a subject suffering from NAFLD or NASH, or suffering from any related symptoms and/or associated pathologies thereof, comprising administering to said subject a functional food additive or a nutraceutical composition comprising any of the compounds covered by general formula I, II or III, and any food grade acceptable salt thereof.

Still most preferred compounds for use in the prevention and/or treatment of NAFLD or NASH, and related symptoms and/or associated pathologies thereof, according to the present invention are selected among compounds: 4a, 5a, 7a, 17a, 17b, 17c, 21a, 21b, 21c, 21d, 21e, 21f, 23a, 23b, 23c, 23d, 23e, 23f, 26a or 26b, as shown in Table 1.

The invention also comprises a compound selected independently from 4a, 5a, 7a, 17a, 17b, 17c, 21a, 21b, 21c, 21d, 21e, 21f, 23a, 23b, 23c, 23d, 23e, 23f, 26a or 26b, as shown in Table 1, or any pharmaceutical composition comprising the same, for use in the prevention and/or treatment of NAFLD or NASH, and related symptoms and/or associated pathologies thereof.

More preferably a compound selected independently from 4a, 5a and 7a, or any pharmaceutical composition comprising the same, for use in the prevention and/or treatment of NAFLD or NASH, and related symptoms and/or associated pathologies thereof.

More preferably a compound selected independently from 4a, 26a, 21a, 26b, 21b, 21c, 21e, 21d, 17a, 17c, 17b or 21f, or any pharmaceutical composition comprising the same, for use in the prevention and/or treatment of NAFLD or NASH, and related symptoms and/or associated pathologies thereof.

More preferably a compound selected independently from 4a, 5a, 7a, 23b, 23c, 26a, 23a, 23e, 23d, 26b, 21d, 17a, 17c, 17b or 23f, or any pharmaceutical composition comprising the same, for use in the prevention and/or treatment of NAFLD or NASH, and related symptoms and/or associated pathologies thereof.

More preferably a compound selected independently from 4a, 26a, 26b, 17a, 17c or 17b, or any pharmaceutical composition comprising the same, for use in the prevention and/or treatment of NAFLD or NASH, and related symptoms and/or associated pathologies thereof.

More preferably a compound selected independently from 4a or 5a, or any pharmaceutical composition comprising the same, for use in the prevention and/or treatment of NAFLD or NASH, and related symptoms and/or associated pathologies thereof. More preferably the compounds for use according to present invention are the hydrochloride salt of 4a or 5a.

More preferably a compound selected independently from 4a, or any pharmaceutical composition comprising the same, for use in the prevention and/or treatment of NAFLD or NASH, and related symptoms and/or associated pathologies thereof. More preferably the compound for use according to present invention is the hydrochloride salt of 4a.

Additionally, the invention comprises a method of preventing and/or treating a subject suffering from NAFLD or NASH, or suffering from any related symptoms and/or associated pathologies thereof, comprising administering to said subject an effective quantity of 4a, 5a, 7a, 17a, 17b, 17c, 21a, 21b, 21c, 21d, 21e, 21f, 23a, 23b, 23c, 23d, 23e, 23f, 26a or 26b, as shown in Table 1, or of pharmaceutical, food additive or nutraceutical compositions comprising the same. More preferably, comprising administering to said subject an effective quantity of 4a, 5a and 7a; or of 4a, 26a, 21a, 26b, 21b, 21c, 21e, 21d, 17a, 17c, 17b or 21f; or of 4a, 5a, 7a, 23b, 23c, 26a, 23a, 23e, 23d, 26b, 21d, 17a, 17c, 17b or 23f; or of 4a, 26a, 26b, 17a, 17c or 17b; or of 4a or 5a.

More preferably the invention comprises a method of preventing and/or treating a subject suffering from NAFLD or NASH, or suffering from any related symptoms and/or associated pathologies thereof, comprising administering to said subject an effective quantity of 4a or of pharmaceutical, food additive or nutraceutical compositions comprising the same.

The invention also includes pharmaceutical compositions, functional food additives or nutraceutical compositions comprising at least one compound selected independently from 4a, 5a, 7a, 17a, 17b, 17c, 21a, 21b, 21c, 21d, 21e, 21f, 23a, 23b, 23c, 23d, 23e, 23f, 26a or 26b, as shown in Table 1, or their pharmaceutically, or food grade, acceptable or allowable, salts and combinations thereof, optionally with any inert ingredient, carrier, excipient or alike for use in the prevention and/or treatment of NAFLD or NASH, and related symptoms and/or associated pathologies thereof. More preferably comprising at least one compound selected independently from 4a, 5a and 7a; or from 4a, 26a, 21a, 26b, 21b, 21c, 21e, 21d, 17a, 17c, 17b or 21f; or from 4a, 5a, 7a, 23b, 23c, 26a, 23a, 23e, 23d, 26b, 21d, 17a, 17c, 17b or 23f; or from 4a, 26a, 26b, 17a, 17c or 17b; or from 4a or 5a.

In a preferred embodiment, the invention includes a pharmaceutical composition, functional food additive or nutraceutical composition comprising 4a, and their pharmaceutically, or food grade, acceptable or allowable, salts and combinations thereof, optionally with any inert ingredient, carrier, excipient or alike for use in the prevention and/or treatment of NAFLD or NASH, and related symptoms and/or associated pathologies thereof.

TABLE 1

| Compound | Structure | Name |
|---|---|---|
| 4a | (β-carboline with 1-(4-methoxyphenyl) and 3-C(O)NH-CH₂CH₂-NH₂) | N(-ethylamine)-1-benzosubstituted-β-carboline-3-carboxamide |
| 5a | (β-carboline with 1-(4-methoxyphenyl) and 3-C(O)NH-CH₂CH₂CH₂-NH₂) | N(-propylamine)-1-benzosubstituted-β-carboline-3-carboxamide |
| 7a | (β-carboline with 1-(4-methoxyphenyl) and 3-C(O)NH-N=CH-phenyl) | 3-(carbohydrazyl-N'-phenylsubstitute)-1-benzosubstitute-β-carbolinic-3-carbohydrazide |
| 23b | (β-carboline with 1-(4-methoxyphenyl) and 3-C(O)NH-CH₂CH₂-N(CH₃)₂ · HCl) | N-(2-dimethylaminoethyl)-1-(4-methoxyphenyl)-9H-pyrido[3,4-b]indole-3-carboxamide hydrochloride |

TABLE 1-continued
| Compound | Structure | Name |
|---|---|---|
| 23c | 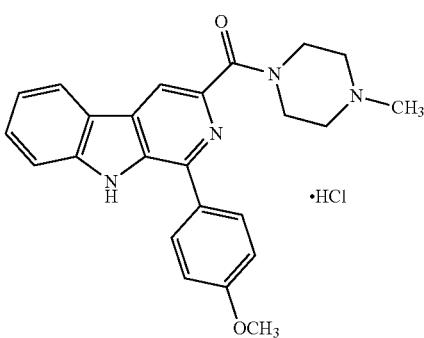 [SMILES: COc1ccc(-c2nc(C(=O)N3CCN(C)CC3)cc3c2[nH]c2ccccc23)cc1 ; Cl] | [1-(4-methoxyphenyl)-9H-pyrido[3,4-b]indol-3-yl]-(4-methylpiperazin-1-yl) methanone hydrochloride |
| 26a | 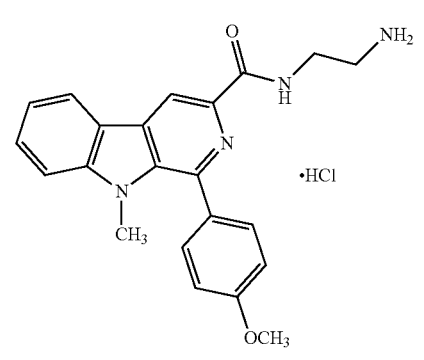 [SMILES: COc1ccc(-c2nc(C(=O)NCCN)cc3c4ccccc4n(C)c23)cc1 ; Cl] | N-(2-aminoethyl)-1-(4-methoxyphenyl)-9-methyl-pyrido[3,4-b]indole-3-carboxamide hydrochloride |
| 21a | 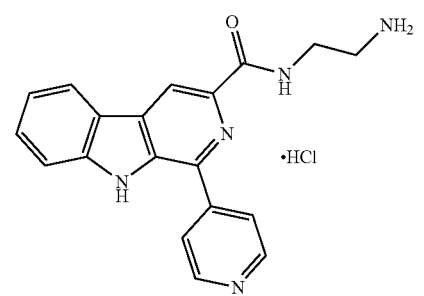 [SMILES: NCCNC(=O)c1cc2c([nH]c3ccccc32)c(-c2ccncc2)n1 ; Cl] | N-(2-aminoethyl)-1-(4-pyridyl)-9H-pyrido[3,4-b]indole-3-carboxamide hydrochloride |
| 23a | 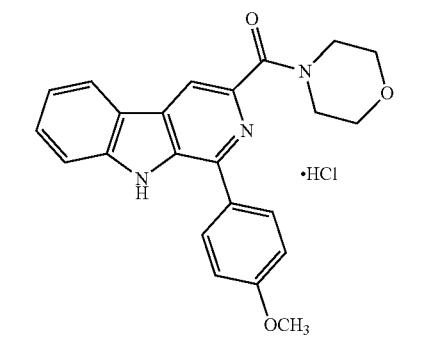 [SMILES: COc1ccc(-c2nc(C(=O)N3CCOCC3)cc3c2[nH]c2ccccc23)cc1 ; Cl] | [1-(4-methoxyphenyl)-9H-pyrido[3,4-b]indol-3-yl]-4-morpholinyl-Methanone Hydrochloride |

TABLE 1-continued

| Compound | Structure | Name |
|---|---|---|
| 23e | 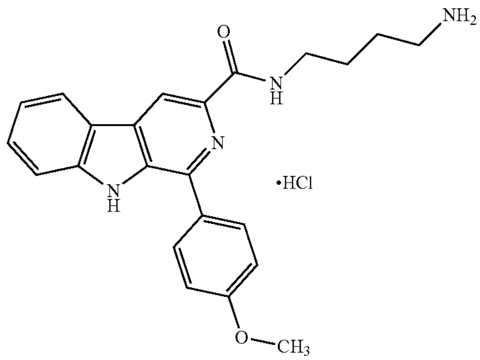 [SMILES: COc1ccc(-c2nc(C(=O)NCCCCN)cc3c2[nH]c2ccccc23)cc1 ; Cl] | N-(4-aminobutyl)-1-(4-methoxyphenyl)-9H-pyrido[3,4-b]indole-3-carboxamide hydrochloride |
| 23d | 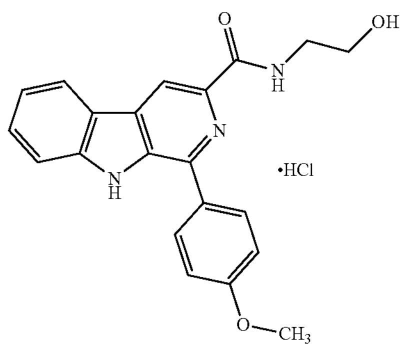 [SMILES: COc1ccc(-c2nc(C(=O)NCCO)cc3c2[nH]c2ccccc23)cc1 ; Cl] | N-(2-hydroxyethyl)-1-(4-methoxyphenyl)-9H-pyrido[3,4-b]indole-3-carboxamide hydrochloride |
| 26b | 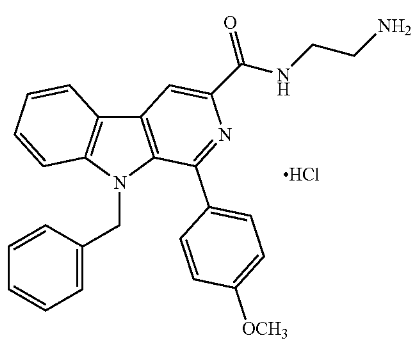 [SMILES: COc1ccc(-c2nc(C(=O)NCCN)cc3c4ccccc4n(Cc4ccccc4)c23)cc1 ; Cl] | N-(2-aminoethyl)-9-benzyl-1-(4-methoxyphenyl)pyrido[3,4-b]indole-3-carboxamide hydrochloride |
| 21b | 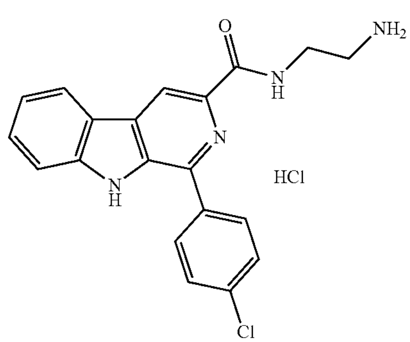 [SMILES: NCCNC(=O)c1cc2c([nH]c3ccccc32)c(-c2ccc(Cl)cc2)n1 ; Cl] | N-(2-aminoethyl)-1-(4-chlorophenyl)-9H-pyrido[3,4-b]indole-3-carboxamide hydrochloride |

TABLE 1-continued

| Compound | Structure | Name |
|---|---|---|
| 21c | 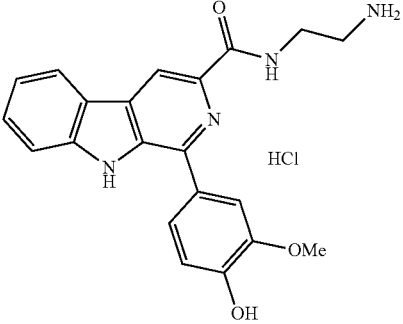 [SMILES: COc1cc(-c2nc(C(=O)NCCN)cc3c2[nH]c2ccccc23)ccc1O ; Cl] | N-(2-aminoethyl)-1-(4-hydroxy-3-methoxy-phenyl)-9H-pyrido[3,4-b]indole-3-carboxamide hydrochloride |
| 21e | 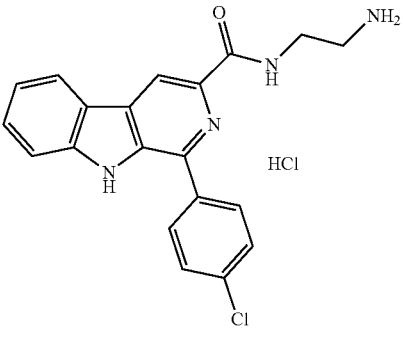 [SMILES: NCCNC(=O)c1cc2c([nH]c3ccccc32)c(-c2ccc(Cl)cc2)n1 ; Cl] | N-(2-aminoethyl)-1-[4-(trifluoromethyl)phenyl]-9H-pyrido[3,4-b]indole-3carboxamide hydrochloride |
| 21d | 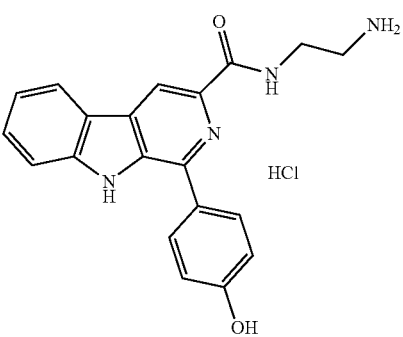 [SMILES: NCCNC(=O)c1cc2c([nH]c3ccccc32)c(-c2ccc(O)cc2)n1 ; Cl] | N-(2-aminoethyl)-1-(4-hydroxyphenyl)-9H-pyrido[3,4-b]indole-3-carboxamide hydrochloride |
| 17a | 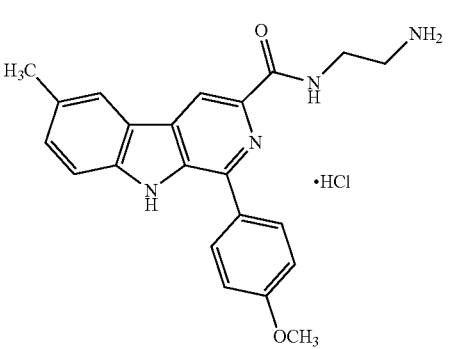 [SMILES: COc1ccc(-c2nc(C(=O)NCCN)cc3c2[nH]c2ccc(C)cc23)cc1 ; Cl] | N-(2-aminoethyl)-6-methyl-1-(4-methoxyphenyl)-9H-pyrido[3,4-b]indole-3-carboxamide hydrochloride |

TABLE 1-continued

| Compound | Structure | Name |
|---|---|---|
| 17c | 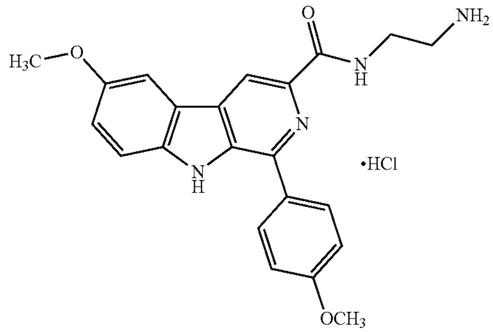 [SMILES: COc1ccc(-c2nc(C(=O)NCCN)cc3c2[nH]c2ccc(OC)cc23)cc1 ; Cl] | N-(2-aminoethyl)-6-methoxy-1-(4-methoxyphenyl)-9H-pyrido[3,4-b]indole-3-carboxamide hydrochloride |
| 17b | 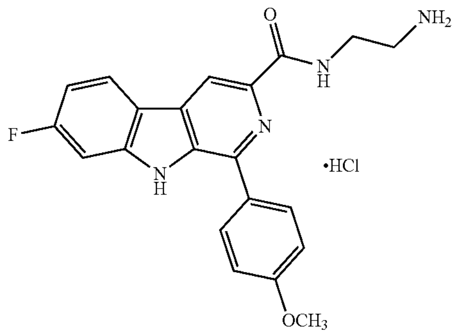 [SMILES: COc1ccc(-c2nc(C(=O)NCCN)cc3c2[nH]c2cc(F)ccc23)cc1 ; Cl] | N-(2-aminoethyl)-7-fluoro-1-(4-methoxyphenyl)-9H-pyrido[3,4-b]indole-3-carboxamide hydrochloride |
| 21f | 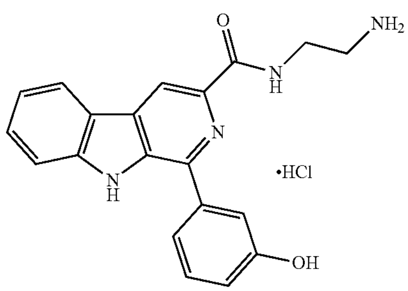 [SMILES: NCCNC(=O)c1cc2c([nH]c3ccccc32)c(-c2cccc(O)c2)n1 ; Cl] | N-(2-aminoethyl)-1-(3-hydroxyphenyl)-9H-pyrido[3,4-b]indole-3-carboxamide hydrochloride |
| 23f | 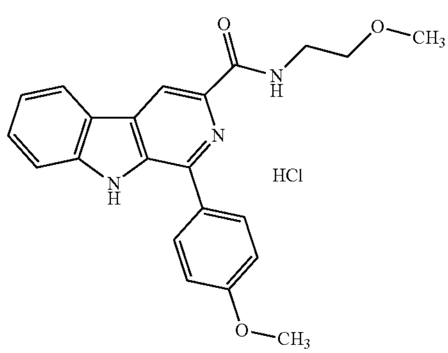 [SMILES: COCCNC(=O)c1cc2c([nH]c3ccccc32)c(-c2ccc(OC)cc2)n1 ; Cl] | N-(2-methoxyethyl)-1-(4-methoxyphenyl)-9H-pyrido[3,4-b]indole-3-carboxamide hydrochloride |

Present invention also covers all intermediate compounds in the synthesis of compounds of the previously described compounds of Table 1, for use in the prevention and/or treatment of NAFLD or NASH, and related symptoms and/or associated pathologies thereof.

Particularly, the invention covers intermediate compounds selected from: 1a, 1b, 2a, 2b, 3a, 3b, 6a, 6b, 7b, 8, 13a, 13b, 13c, 14a, 14b, 14c, 15a, 15b, 15c, 16a, 16b, 16c, 18a, 18b, 18c, 18d, 18e, 18f, 19a, 19b, 19c, 19d, 19e, 19f, 20a, 20b, 20c, 20d, 20e, 20f, 22a, 22b, 22c, 22d, 22e, 22f, 24a, 24b, 25a, or 25b, for use in the prevention and/or treatment of NAFLD or NASH, and related symptoms and/or associated pathologies thereof, and also comprises the invention a method for preventing and/or treating a subject suffering from NAFLD or NASH, or suffering from any related symptoms and/or associated pathologies thereof, comprising administering to said subject said intermediate compounds, or of pharmaceutical, food additive or nutraceutical compositions comprising the same.

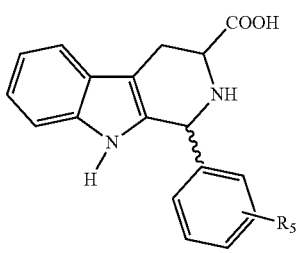
(1a) R₅ = p-OCH₃ (p = "para" position)
(1b) R₅ = H
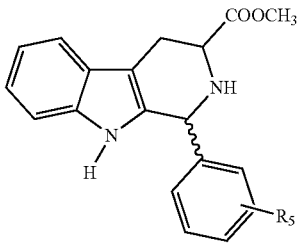
(2a) R₅ = p-OCH₃
(2b) R₅ = H
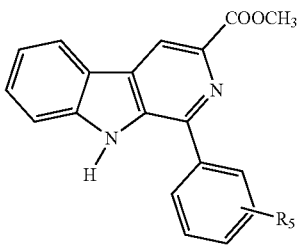
(3a) R₅ = p-OCH₃
(3b) R₅ = H
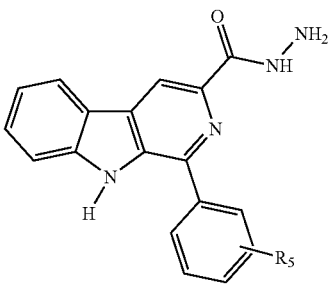
(6a) R₅ = p-OCH₃
(6b) R₅ = H
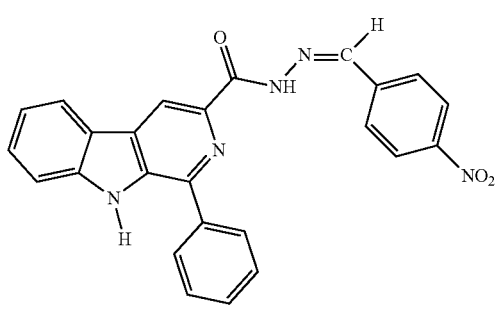
7b
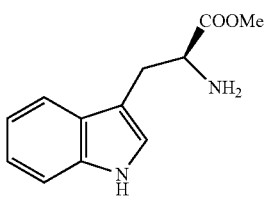
(8)
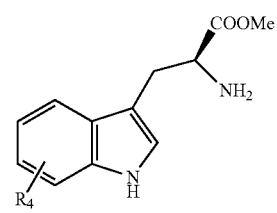
(13a) R₄: 5-CH3
(13b) R₄: 6-F
(13c) R₄: 7-F
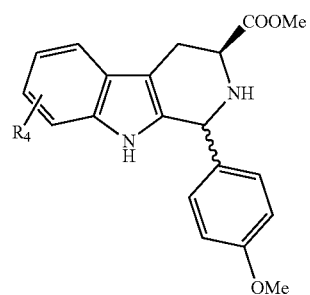
(14a)
R₄: 5-CH3
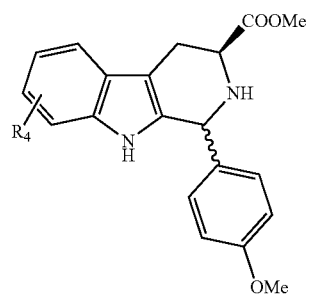
(14b)
R₄: 6-F
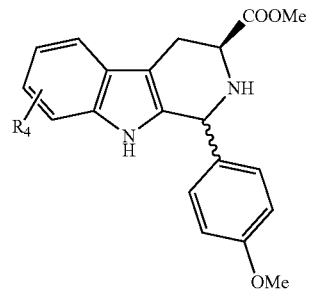
(14c)
R₄: 6-OCH³

-continued
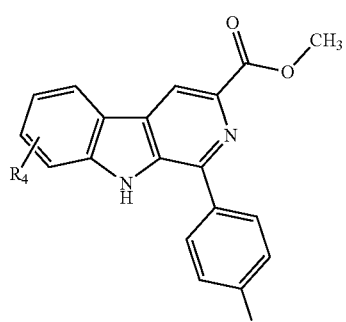
R$_4$: 5-CH$_3$
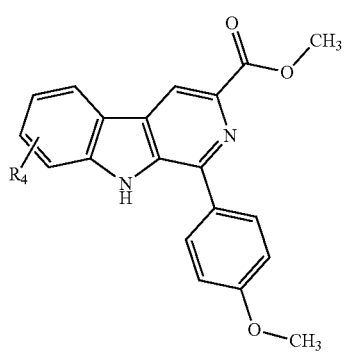
R$_4$: 6-F
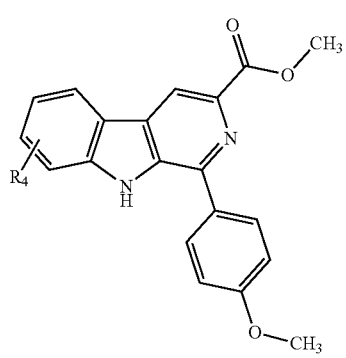
R$_4$: 6-OCH$_3$
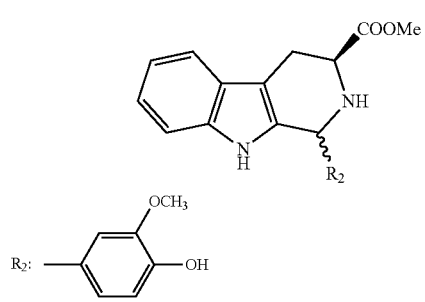
(18c)
R$_2$:
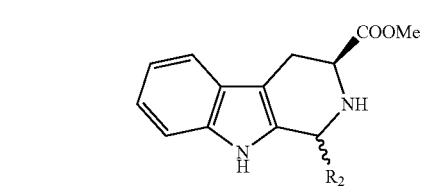
(18d)
-continued
(15a)
R$_2$:
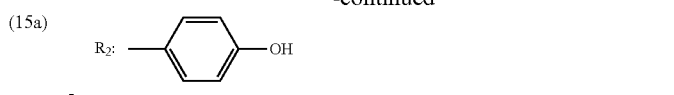
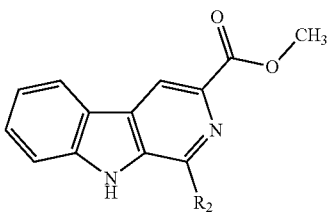
(19c)
(15b)
R$_2$:
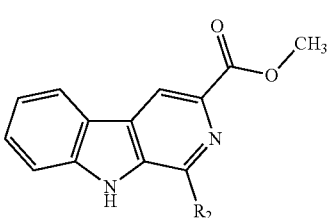
(19d)
R$_2$:
(15c)
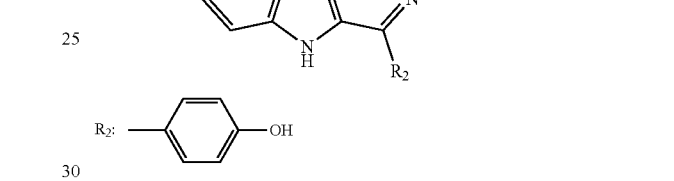
(16a)
R$_4$: 5-CH$_3$
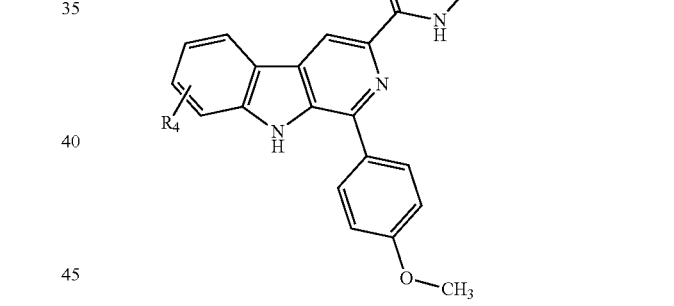
HCl
(16b)
R$_4$: 6-F -continued
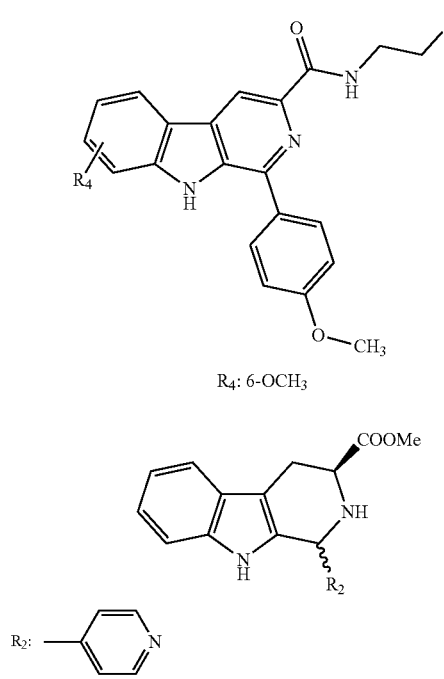
(16c)
R4: 6-OCH3
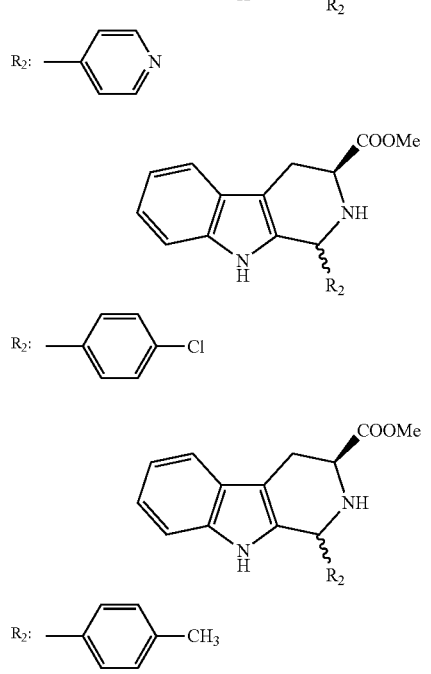
(18a)
R2: 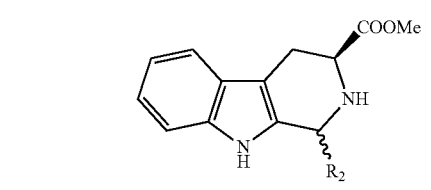
(18b)
(18e)
(18f)
R2: 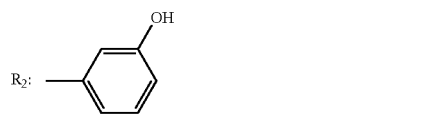
-continued
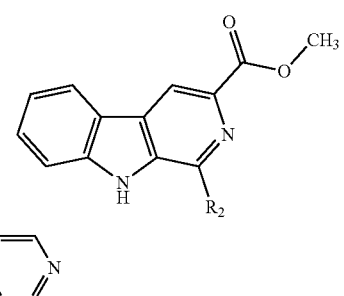
(19a)
R2:
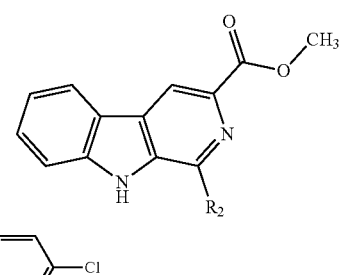
(19b)
R2:
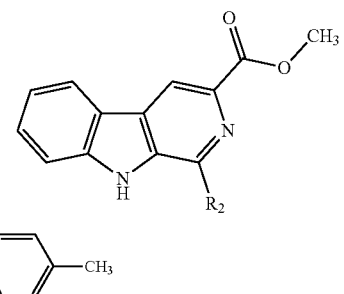
(19e)
R2:
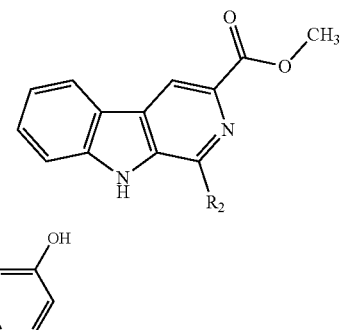
(19f)
R2:
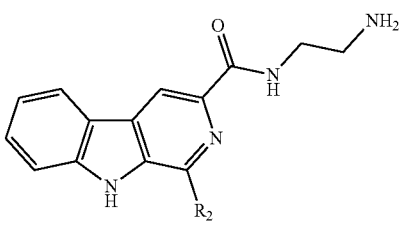
(20a)
R2: 

-continued
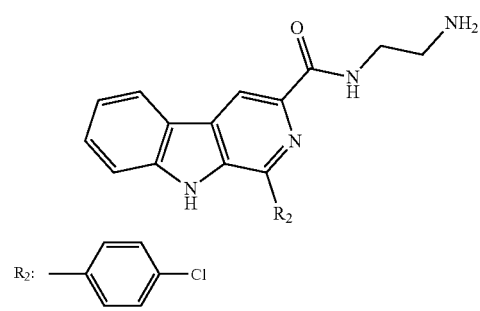
(20b)
R$_2$: ⟨4-Cl-phenyl⟩
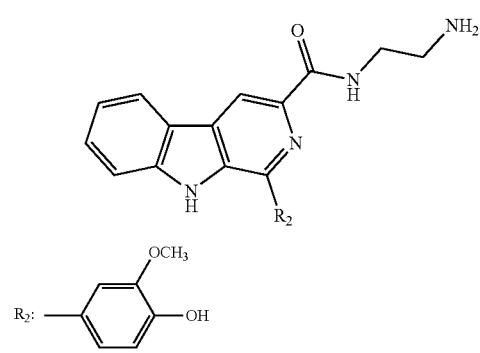
(20c)
R$_2$: ⟨3-OCH$_3$, 4-OH phenyl⟩
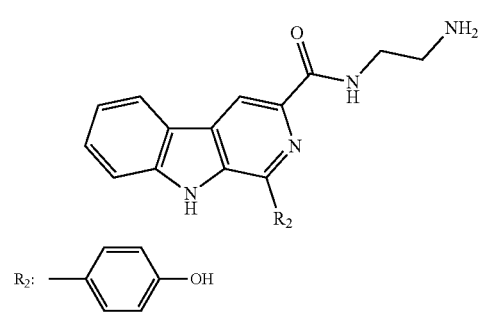
(20d)
R$_2$: ⟨4-OH phenyl⟩
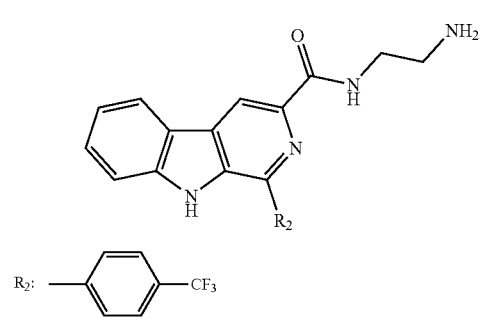
(20e)
R$_2$: ⟨4-CF$_3$ phenyl⟩
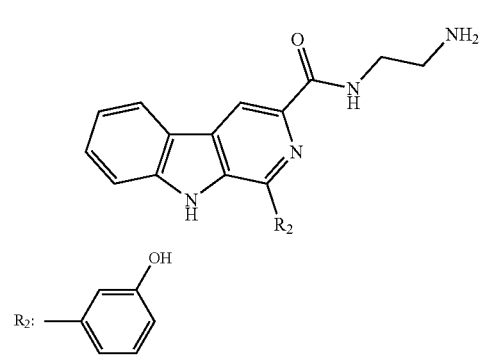
(20f)
R$_2$: ⟨3-OH phenyl⟩
-continued
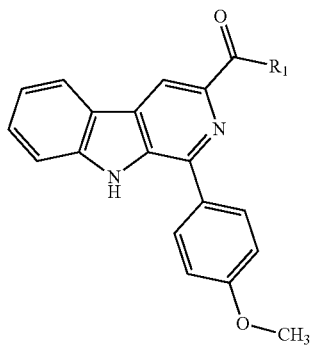
(22a)
R$_1$: ⟨morpholinyl⟩
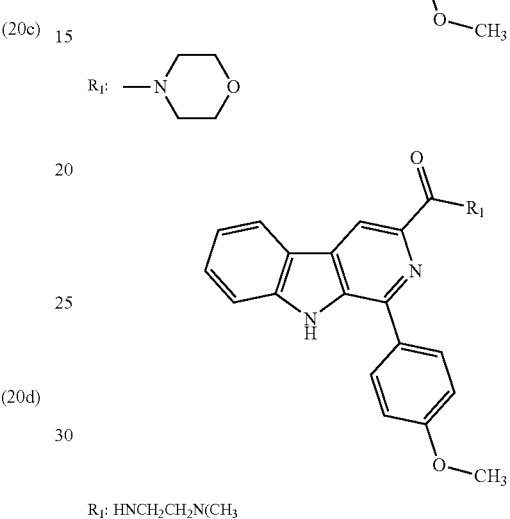
(22b)
R$_1$: HNCH$_2$CH$_2$N(CH$_3$)$_2$
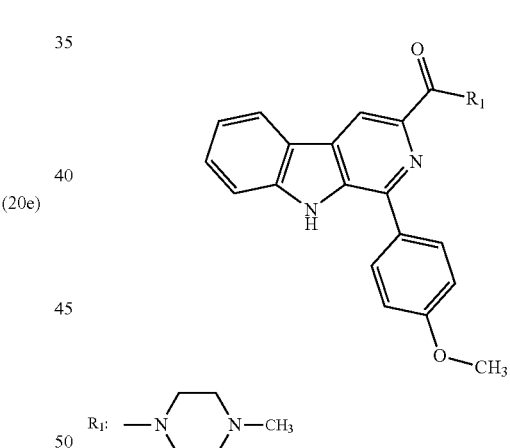
(22c)
R$_1$: ⟨4-methylpiperazinyl⟩
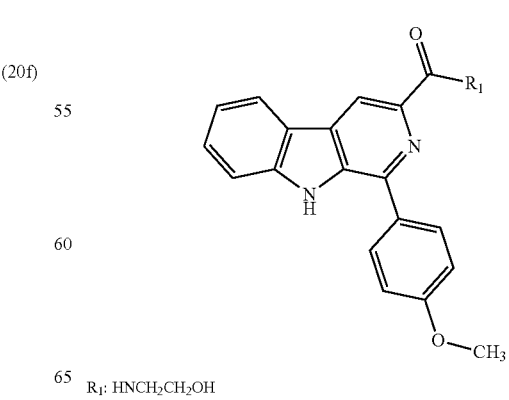
(22d)
R$_1$: HNCH$_2$CH$_2$OH

33
-continued (22e)

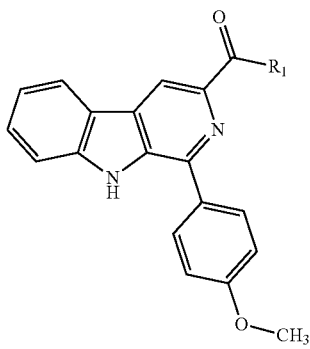

R<sub>1</sub>: HN—(CH<sub>2</sub>)<sub>4</sub>—NH<sub>2</sub>

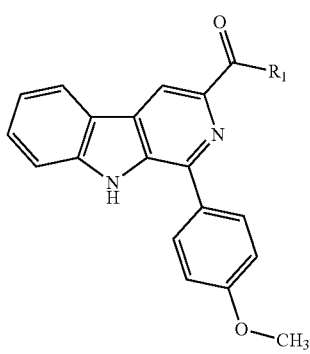

R<sub>1</sub>: HNCH<sub>2</sub>CH<sub>2</sub>OCH<sub>3</sub>

(24a)

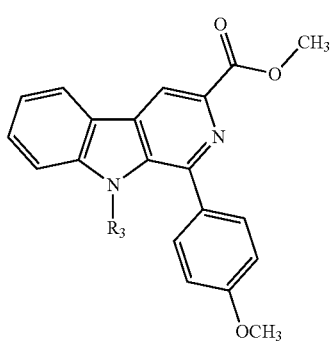

R<sub>3</sub>: CH<sub>3</sub>

(24b)

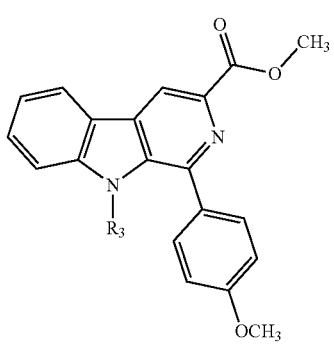

R<sub>3</sub>: CH<sub>2</sub>Ph

34
-continued (22f)

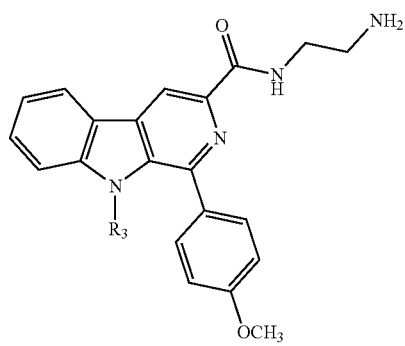

(25a)

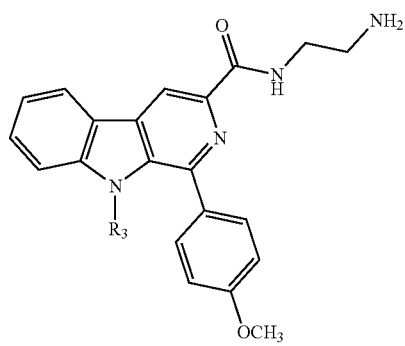

R<sub>3</sub>: CH<sub>3</sub> or (25b)

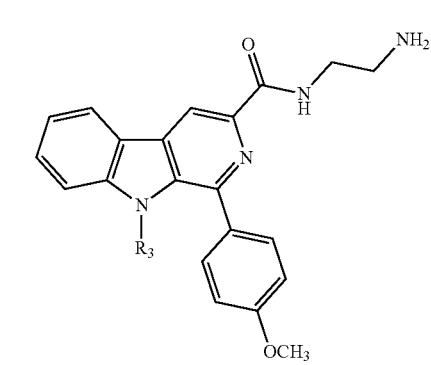

R<sub>3</sub>: CH<sub>2</sub>Ph

Particularly, the invention covers intermediate compounds selected from: 7b, 15a, 15b, 15c, 16a, 16b, 16c, 19a, 19b, 19c, 19d, 19e, 19f, 20a, 20b, 20c, 20d, 20e, 20f, 22a, 22b, 22c, 22d, 22e, 22f, 24a, 24b, 25a, or 25b, for use in the prevention and/or treatment of NAFLD or NASH, and related symptoms and/or associated pathologies thereof, and also comprises the invention a method for preventing and/or treating a subject suffering from NAFLD or NASH, or suffering from any related symptoms and/or associated pathologies thereof, comprising administering to said subject said intermediate compounds, or of pharmaceutical, food additive or nutraceutical compositions comprising the same.

Particularly, the invention covers intermediate compounds selected from: 7b, 16a, 16b, 16c, 20a, 20b, 20c, 20d, 20e, 20f, 22a, 22b, 22c, 22d, 22e, 22f, 24a, 24b, 25a, or 25b for use in the prevention and/or treatment of NAFLD or NASH, and related symptoms and/or associated pathologies thereof, and also comprises the invention a method for preventing and/or treating a subject suffering from NAFLD or NASH, or suffering from any related symptoms and/or associated pathologies thereof, comprising administering to said subject said intermediate compounds, or of pharmaceutical, food additive or nutraceutical compositions comprising the same.

Preferably, the invention also comprises compounds named as: 4a, 5a, 7a, 21a, 21b, 21e, 23a, 23b, 23d, 23e, 23f or 26b, taken alone or in combinations thereof, or pharmaceutical compositions comprising the same, are particularly suitable for use in the treatment or prevention of NAFLD or NASH, and related symptoms and/or associated pathologies thereof, or for use in manufacturing a medicament for the treatment or prevention of NAFLD or NASH, and related symptoms and/or associated pathologies thereof.

The invention also comprises any of the compounds covered by general formula I, II or III as previously disclosed, or any functional food additive or nutraceutical composition comprising the same, for use as food functional additive or nutraceutic particularly for preventing or for reducing the symptoms related to NAFLD or NASH, and related pathologies thereof.

Preferably, the invention also comprises compounds named as: 4a, 5a, 7a, 21a, 21b, 21e, 23a, 23b, 23d, 23e, 23f or 26b, taken alone or in combinations thereof, or any functional food additive or nutraceutical composition comprising the same, they are particularly suitable for use as food functional additive or nutraceutic particularly for preventing or for reducing the symptoms related to NAFLD or NASH, and related pathologies thereof.

Additionally, the invention also comprises a method for preventing or for reducing the symptoms related to NAFLD or NASH, and related pathologies thereof, in a subject suffering from said symptoms and related pathologies, comprising the administration of an effective amount of any of the compounds covered by general formula I, II or III as previously disclosed, or any functional food additive or nutraceutical composition comprising the same, to said subject.

BRIEF DESCRIPTION OF THE FIGURES

FIG. 2: In vivo efficacy of the compounds of the invention in decreasing liver fat. FIG. 2A, shows the cholesterol liver content in DIO mice treated with a hydrochloride salt of compound 4a (SJT4A) and with compound 7a (SJT7A) during 36 days (both 50 mg/kg) versus a control treated with saline solution (0.9% NaCl) and a positive control treated with metformin (150 mg/kg). FIG. 2B shows the hepatic triglycerides levels in DIO mice treated with a hydrochloride salt of compound 4a (SJT4A) and with compound 7a (SJT7A) during 36 days (both 50 mg/kg) versus a control treated with saline (0.9% NaCl) and a positive control treated with metformin (150 mg/kg).

EXAMPLES

Figure 1:
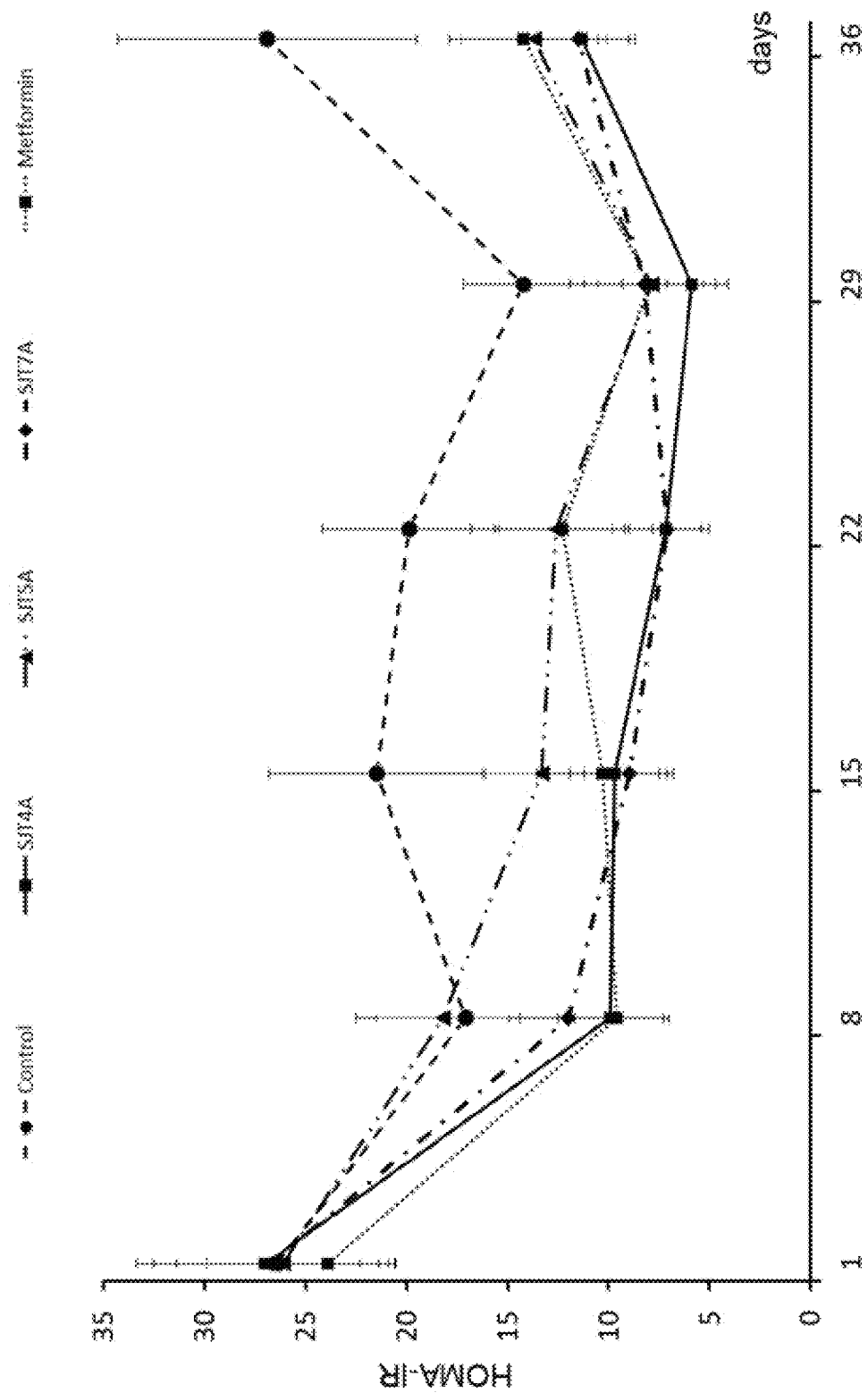
FIG. 1: In vivo efficacy of the hydrochloride salts of the compounds 4a (SJT4A) and 5a (SJT5A); and of compound 7a (SJT7A), all with a 50 mg/kg dosage, in decreasing insulin resistance (HOMA-IR) in a DIO model mice during a 36 days treatment versus a control treated with saline solution (0.9% NaCl) and a positive control treated with metformin (150 mg/kg).

Example 1: In Vivo Effect of the Compounds of the Invention Decreasing Insulin Resistance As mentioned herein above, insulin resistance has been recognized as a key manifestation or symptom related to the development of NAFLD.

To assess the performance of the compounds disclosed in decreasing insulin resistance, DIO mice (C57Bl/6J male mice) were treated with hydrochloride salts of compounds 4a, 5a; and with compound 7a during 36 days, versus a control treated with saline (0.9% NaCl) and versus DIO mice treated with metformin as a positive control.

For the assessment, 60 C57Bl/6 J male mice (16-week-old at delivery and 40 g of average weight), obtained from Charles River France put on high fat diet for 10 weeks. The animals were housed in ventilated and enriched housing cages (310×125×127 mm$^3$) throughout the experimental phase. Animals' cages litters were changed at least once a week. Mice were housed in groups of 10 mice on a normal 12 hours light cycle (at 08:00 pm lights were switched off), at 22±2° C. and 50±10% relative humidity. After reception, mice were maintained for three additional acclimation weeks. During the whole test (acclimation+treatment phase) a high fat diet (D12492 purchased from Research Diet Inc.; 60% fat) and tap water were provided ad libitum.

After the acclimation period, mice were fasted for 6 hours and blood glucose and plasma insulin were measured. Ten animals, those with lower blood glucose/plasma insulin, were discarded from the study. Then, the others were randomized into 5 homogenous groups (n=10 mice per group) according to their blood glucose/plasma insulin levels (HOMA-IR or Homeostatic model assessment-insulin resistance index) and body weight.

Mice were treated orally twice daily for 36 days with either saline solution (control group), a test compound (4a, 5a, 7a; 50 mg/kg) or metformin (150 mg/kg).

Body weight were weekly measured as well as blood glucose and plasma insulin after a 6 hour-fasting.

Blood glucose was measured by sampling blood from the tip of the tail: a drop of blood is collected and placed on a glucometer strip (Accu-Check® glucometer, Roche, Switzerland). Plasma insulin was detected via ELISA (Elisa Kit, Eurobio, France) using 5 µl samples.

The Homeostatic model assessment-insulin resistance index (HOMA-IR), which is used to quantify insulin resistance, was calculated from fasting blood glucose, and plasma insulin values as follows: HOMA-IR=(mM glucose× µU/mL insulin)/22.5, being this constant a normalizing factor (Matthews et al., 1985, Diabetologia 28(7), 412-9).

FIG. 1 shows the HOMAR-IR results for the mice treated with each of the compounds tested, for mice treated with metformin, and also for the control animals, after 1, 8, 15, 22, 29 and 36 days. Mice treated with hydrochloride salts of compounds 4a and 5a; and with compound 7a, showed lower insulin resistance compared to the control animals and similar to the animals treated with metformin, during the whole duration of the treatment.

Data expressed as mean±s.e.m. values from 10 animals.

Example 2: In Vivo Effect on Liver Lipid Content Associated with Hepatic Steatosis of the Compounds of the Invention 2.1. Effect of Compounds 4a and 7a on Liver Lipid Content: 36 Days Assay in DIO Mice.

To assess the performance of the compounds disclosed in decreasing hepatic lipid content, DIO mice (C57Bl/6 J male mice) were treated with a hydrochloride salt of compound 4a; and with compound 7a during 36 days, versus a control of DIO mice treated with saline (0.9% NaCl) and versus DIO mice treated with Metformin as a positive control.

For the assessment, 60 C57Bl/6 J male mice (16-week-old at delivery and 40 g of average weight), obtained from Charles River France, were put on high fat diet for 10 weeks. The animals were housed in ventilated and enriched housing cages (310×125×127 mm$^3$) throughout the experimental phase. Animals' cages litters were changed at least once a week. Mice were housed in groups of 10 mice on a normal 12 hours light cycle (at 08:00 pm lights were switched off), at 22±2° C. and 50±10% relative humidity. After reception, mice were maintained for three additional acclimation weeks. During the whole assessment (acclimation+treatment phase) a high fat diet (D12492 purchased from Research Diet Inc; 60% fat) and tap water were provided ad libitum.

After the acclimation period, mice were fasted for 6 hours and blood glucose and plasma insulin were measured. Ten animals, those with lower blood glucose/plasma insulin, were discarded from the study. Then, the others were randomized into 5 homogenous groups (n=10 mice per group) according to their blood glucose/plasma insulin levels (HOMA-IR) and body weight. Mice were treated orally twice daily for 36 days with either saline solution (control group), SJT test compound (4a, 7a; 50 mg/kg) or metformin (150 mg/kg).

Finally, mice were sacrificed, and liver was collected, weighted and stored at −80° C. for additional analysis. Liver samples were dissected for liver lipids assay. Liver lipids were assayed using colorimetric commercial assay kits, from liver samples homogenate after lipid solubilization in deoxycholate as described by Miao et al., J Lipid Res, 2004, 45, 1410-17. Samples were homogenized with an ultrasound probe with 500 µl distilled water during few seconds. Then cholic acid at 1% is added to make lipids soluble. The measurement of the different lipids was then performed using colorimetric kits from Sobioda, France.

Figure 2C:
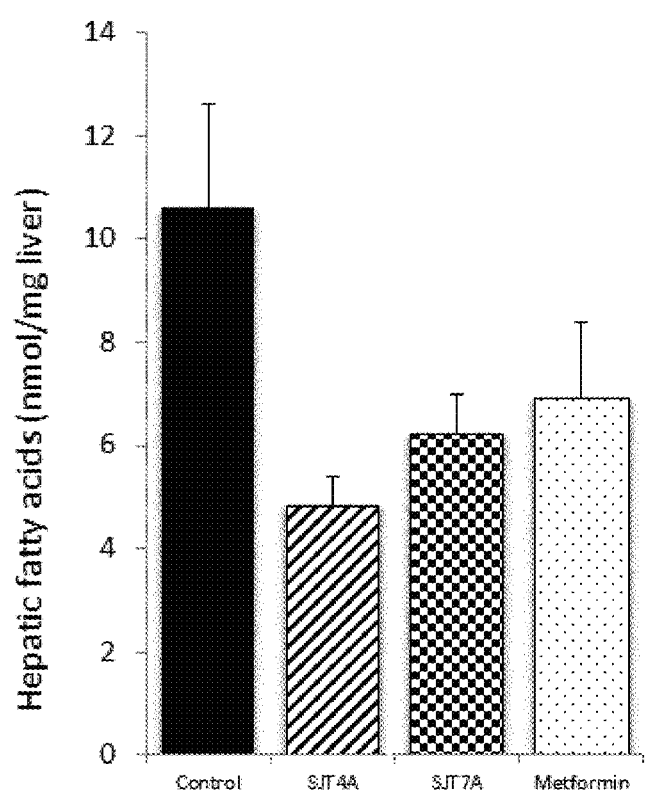
FIG. 2C shows the hepatic fatty acid levels in DIO mice treated with a hydrochloride salt of compound 4a (SJT4A) and with compound 7a (SJT7A) during 36 days (both 50 mg/kg) versus a control treated with saline (0.9% NaCl) and a positive control treated with metformin (150 mg/kg).

FIGS. 2A, 2B and 2C show the levels of hepatic cholesterol, hepatic triglycerides and hepatic fatty acids, respectively, after 36 days of treatment with a hydrochloride salt of compound 4a and with compound 7a. In each case both mice groups treated with compounds 4a and 7a showed lower lipid levels than untreated control animals.

Data expressed as mean±s.e.m. values from 10 animals.

2.2. Effect of a Hydrochloride Salt of Compound 4a on Liver Lipid Content: 8 Weeks Assay in DIO-NASH Mice.

The DIO-NASH mouse model is fed a high fat diet that results on non-alcoholic fat liver disease and are based on C57Bl/6J mice put on a 40% high fat diet prior to the assays. For the assessment of effect of the compounds of the invention in liver lipid content in non-alcoholic fat liver disease, 34 C57Bl/6J male mice (5-week-old at delivery), obtained from Janvier, France, were used. The DIO-NASH mice group were put on high fat diet (40% AMLN diet, D09100301 Research Diets, USA) and a control group (LEAN-CHOW) was put on a regular chow diet (Altromin 1324, Brogaarden, Denmark) for 35 weeks prior to the study.

The animals (kept in single housings) were checked minimum once daily where signs of abnormal behavior, abnormal locomotor activity, ataxia or clinical signs of disease (lack of grooming, raised fur, signs of pain upon handling, loss of excessive body-weight) were followed closely. Health status judged to warrant additional evaluation was examined by a Clinical Veterinarian, or a technician working under the supervision of the Clinical Veterinarian. During the study period the same abnormal behavior and clinical signs of disease were used to determine if animals were not thriving and were terminated for ethical reasons. Any possible veterinarian-recommended treatments were performed following agreement with the Study Director. Mice were housed on a normal 12 hours light cycle (lights off 3 pm) and room environment was controlled (targeted ranges: temperature 21±2° C.; relative humidity 50±10%).

Each animal was uniquely identified by an implantable microchip (Pet ID Microchip, E-vet) upon arrival to the animal unit. Animals were identified using the WS-1 weigh station (MBrose, Denmark) connected to a laptop running the HM02Lab software (Ellegaard Systems, Denmark). The HM02Lab software matches body weight with the animal ID.

For liver biopsies, mice were anesthetized by inhalation anesthesia using isoflurane (2-3%). A small abdominal incision was made in the midline and the left lateral lobe of the liver was exposed. A cone shaped wedge of liver tissue (approximately 50 mg) was excised from the distal portion of the lobe and fixated in 10% neutral buffered formalin (4% formaldehyde) for histology. The cut surface of the liver was instantly electrocoagulated using bipolar coagulation (ERBE VIO 100 electrosurgical unit). The liver was returned to the abdominal cavity, the abdominal wall was sutured, and the skin is closed with staplers. For post-operative recovery mice received carprofen (5 mg/kg) administered subcutaneously on OP day and post-OP day 1 and 2. Tissue samples were stored at −80° C. prior to the histology tests.

2.2.A. Total Fat Content in Liver

To assess the effect of compound 4a on hepatic lipid content in mice with non-alcoholic fat liver disease, DIO-NASH mice (C57Bl/6J male mice) were treated with a hydrochloride salt of compound 4a during 8 weeks (50 mg/kg, p.o., b.i.d.), versus a control of DIO-NASH mice treated with saline (0.9% NaCl) and versus LEAN-CHOW mice also treated with saline (0.9% NaCl), as a positive control. Liver lipid content was determined by morphometry. As mentioned previously, The DIO-NASH mice group were put on high fat diet (40% AMLN diet, D09100301 Research Diets, USA) and a control group (LEAN-CHOW) was put on a regular chow diet (Altromin 1324, Brogaarden, Denmark) for 35 weeks prior to the study.

Figure 3A:
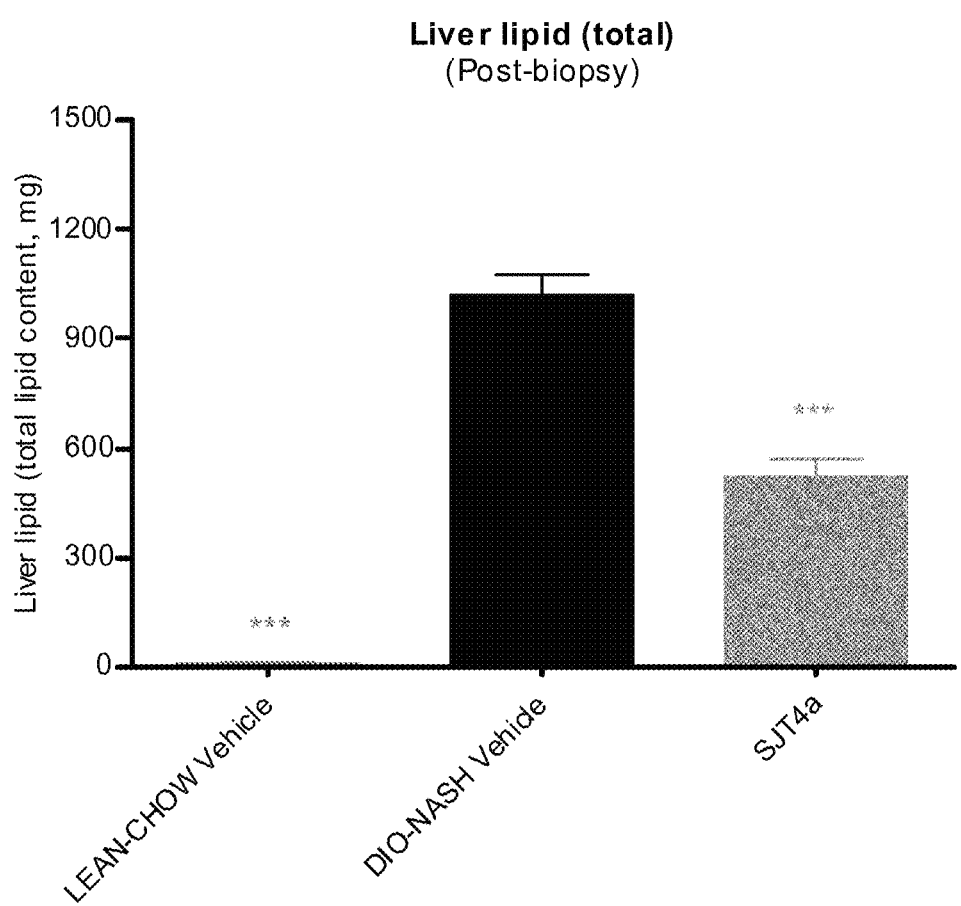
FIG. 3: A shows in vivo effect of a hydrochloride salt of compound 4a (SJT4a) in hepatic lipid content. DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl). B shows representative images of liver morphology for the three previous mice groups at the end of the treatment (magnification ×20).

FIG. 3A shows that, at the end of the assay, DIO-NASH mice control group treated with vehicle (central column) showed an increased liver content compared to the LEAN-CHOW mice control group also treated with vehicle (left column), whereas DIO-NASH mice group treated with a hydrochloride salt of compound 4a (right column) presented a reduced liver lipid content (reduced steatosis) compared to the DIO-NASH mice control group.

Data expressed as mean±s.e.m. values from 10-12 animals, *** $p<0.001$, vs DIO-NASH vehicle; One-way ANOVA with Dunnett's Multiple Comparison Test.

Figure 3B:
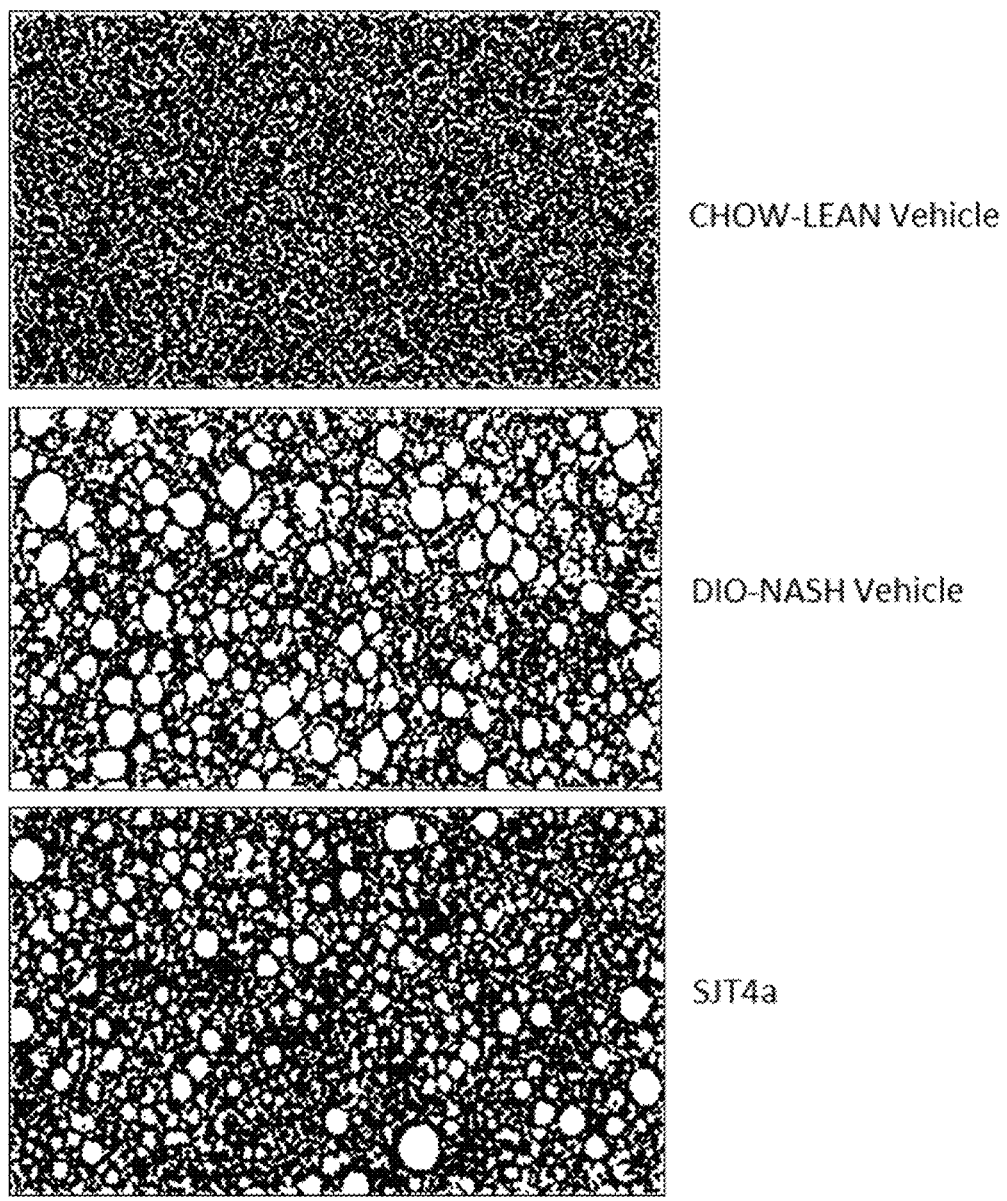

FIG. 3B shows representative images of liver morphology for the three mice groups at the end of the treatment (magnification ×20), where it is seen that the treatment with compound 4a diminished the steatosis in DIO-NASH mice compared to the DIO-NASH mice control group treated with vehicle. The liver samples were Hematoxylin & Eosin (H&E) stained. For that the samples were incubated in Mayer's Hematoxylin (Dako), washed in tap water, stained in Eosin Y solution (Sigma-Aldrich), hydrated, mounted with Pertex and then allowed to dry before scanning.

2.2.B. Triglycerides and Cholesterol Liver Content

To assess the effect of compound 4a on hepatic triglyceride or cholesterol content in animals with non-alcoholic fat liver disease, DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl). The DIO-NASH mice group were put on high fat diet (40% AMLN diet, D09100301 Research Diets, USA) and a control group (LEAN-CHOW) was put on a regular chow diet (Altromin 1324, Brogaarden, Denmark) for 35 weeks prior to the study.

The triglyceride content in liver was determined using the Triglyceride reagent (Cat. no. 22-045-795, Roche Diagnostics, Germany) on a Cobas™ C-501 autoanalyzer. Homogenized liver tissue was heated to 80-100° C. twice, centrifuged in a microcentrifuge and the triglyceride content was measured in the supernatant.

Figure 4A:
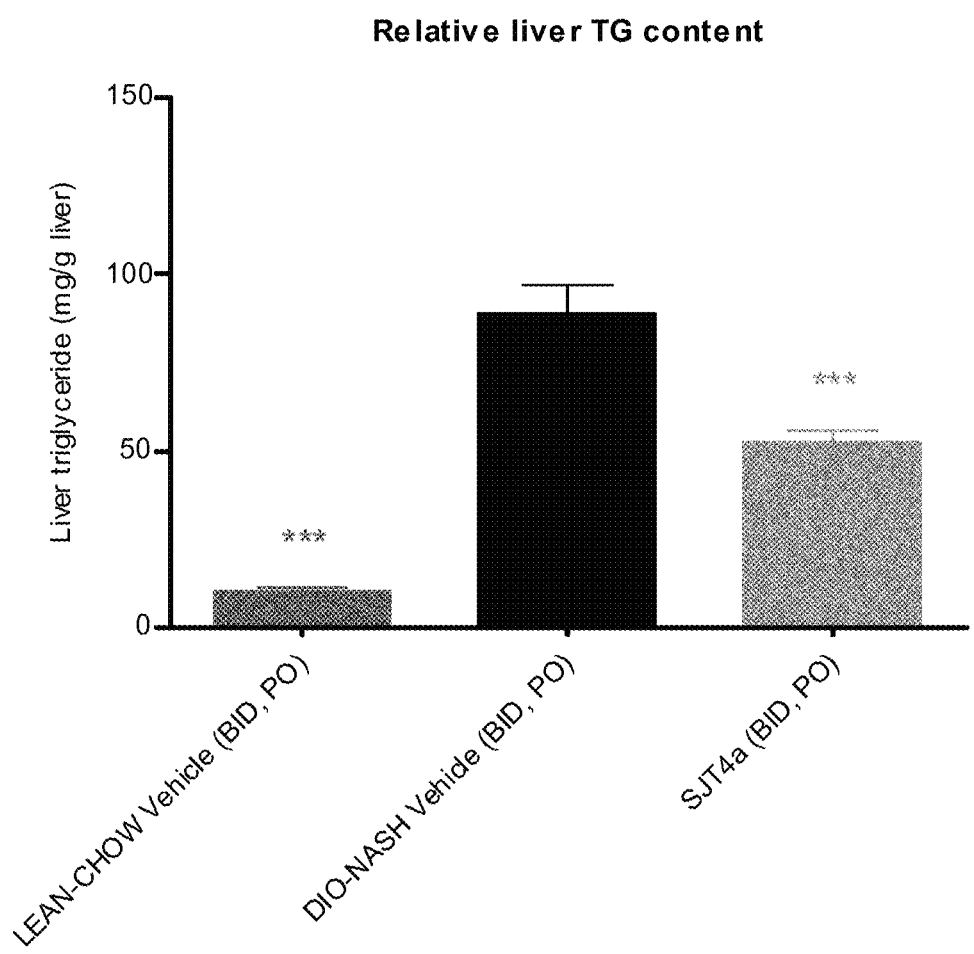
FIG. 4: A shows in vivo effect of a hydrochloride salt of compound 4a (SJT4a) in hepatic triglycerides content. B shows in vivo effect of a hydrochloride salt of compound 4a (SJT4a) in hepatic cholesterol content. In both cases DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl).

FIG. 4A shows that, at the end of the assay, DIO-NASH mice control group treated with vehicle (central column) showed increased liver triglyceride levels compared to the LEAN-CHOW mice control group also treated with vehicle (left column), whereas DIO-NASH mice group treated with a hydrochloride salt of compound 4a (right column) presented reduced liver triglyceride levels compared to the DIO-NASH mice control group.

Data expressed as mean±s.e.m. values from 10-12 animals, *** $p<0.001$, vs DIO-NASH vehicle; One-way ANOVA with Dunnett's Multiple Comparison Test (all columns against DIO-NASH vehicle).

Figure 4B:
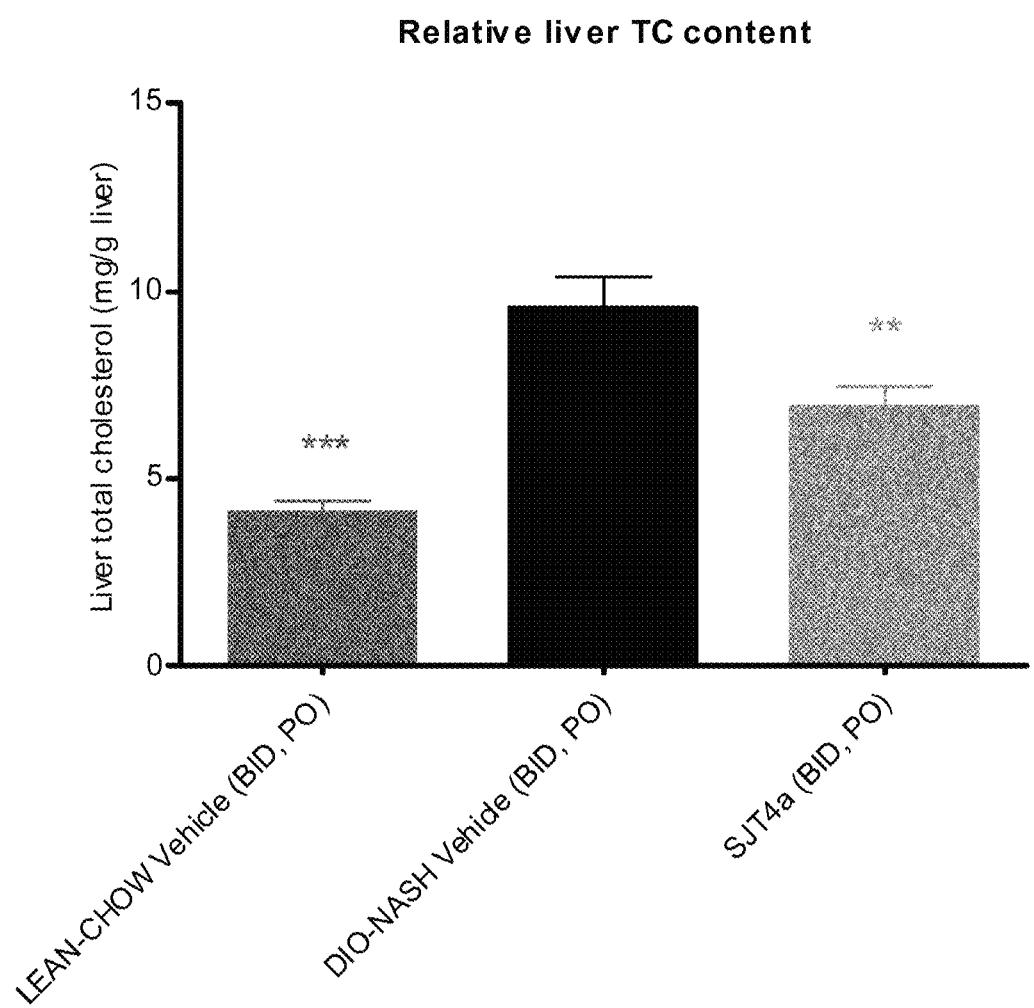

FIG. 4B shows that, at the end of the assay, DIO-NASH mice control group treated with vehicle (central column) showed increased liver cholesterol levels compared to the LEAN-CHOW mice control group also treated with vehicle (left column), whereas DIO-NASH mice group treated with a hydrochloride salt of compound 4a (right column) presented reduced liver cholesterol levels compared to the DIO-NASH mice control group.

Data expressed as mean±s.e.m. values from 10-12 animals,  $p<0.01$, * $p<0.001$, vs DIO-NASH vehicle; One-way ANOVA with Dunnett's Multiple Comparison Test (all columns against DIO-NASH vehicle).

Example 3: In Vivo Effect on Liver Weight of the Compounds of Present Invention 3.1: Effect of Compounds 4a and 5a on Liver Weight: 36 Days Assay in DIO Mice.

To assess the performance of the compounds disclosed decreasing liver overweight, DIO mice (C57Bl/6J male mice) were treated with compounds 4a and 5a during 36 days, versus a control of DIO mice treated with vehicle (0.9% NaCl) and DIO mice treated with Metformin as a positive control.

For the assessment, 60 C57Bl/6J male mice (16-week-old at delivery and 40 g of average weight), obtained from Charles River France, were put on high fat diet for 10 weeks. The animals were housed in ventilated and enriched housing cages (310×125×127 mm$^3$) throughout the experimental phase. Animals' cages litters were changed at least once a week. Mice were housed in groups of 10 mice on a normal 12 hours light cycle (at 08:00 pm lights were switched off), at 22±2° C. and 50±10% relative humidity. After reception, mice were maintained for three additional acclimation weeks. During the whole test (acclimation+treatment phase) a high fat diet (D12492; purchased from Research Diet Inc 60% fat) and tap water were provided ad libitum.

After the acclimation period, mice were fasted for 6 hours and blood glucose and plasma insulin were measured. Ten animals, those with lower blood glucose/plasma insulin, were discarded from the study. Then, the others were randomized into 5 homogenous groups (n=10 mice per group) according to their blood glucose/plasma insulin levels (HOMA-IR) and body weight. Mice were treated orally twice daily for 36 days with either saline solution (control group), SJT test compound (hydrochloride salts of compounds 4a and 5a; 50 mg/kg) or metformin (150 mg/kg).

Finally, mice were sacrificed, and liver was collected, weighted and stored at −80° C. for additional analysis.

Figure 5:
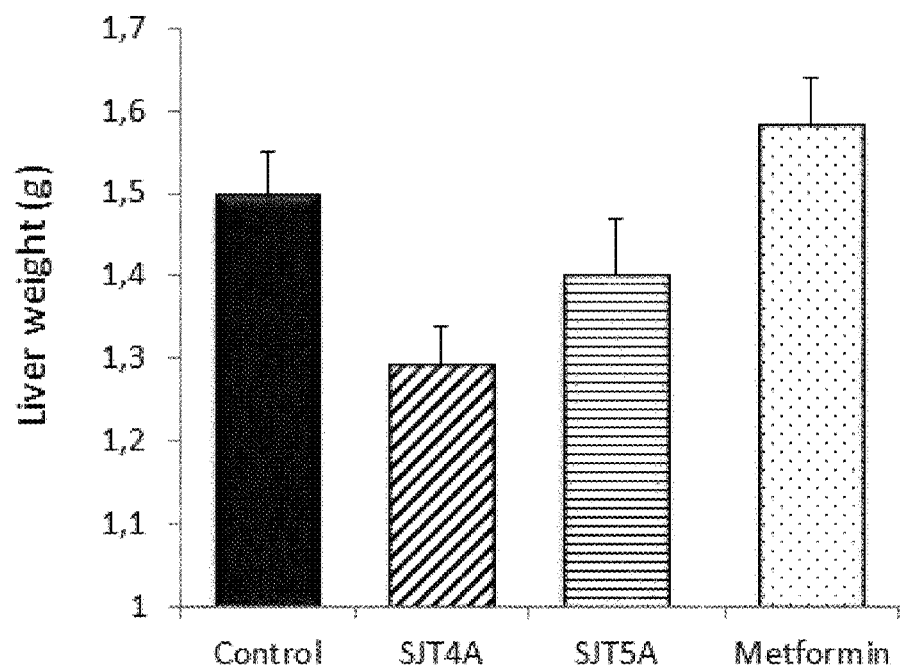
FIG. 5: In vivo efficacy of the hydrochloride salts of compounds 4a (SJT4A) and 5a (SJT5A), both 50 mg/kg, in decreasing liver overweight associated with hepatic steatosis in DIO mice after 36 days of treatment versus a control treated with saline (0.9% NaCl) and a positive control treated with metformin (150 mg/kg).

FIG. 5 shows the liver overweight after 36 days of treatment with hydrochloride salts of compounds 4a and 5a. Both mice groups treated with hydrochloride salts of compounds 4a and 5a show lower liver weight than either mice treated with metformin or than the control animals.

Data expressed as mean±s.e.m. values from 10 animals.

3.2. Effect of Compound 4a on Liver Weight: 8 Weeks Assay in DIO-NASH Mice.

The animals were kept and examined under the same conditions were used as in example 2.2. The liver biopsies were also carried out under the same conditions as in example 2.2.

To assess the effect of compound 4a on liver weight of mice with non-alcoholic fat liver disease, DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl). The DIO-NASH mice group were put on high fat diet (40% AMLN diet, D09100301 Research Diets, USA) and a control group (LEAN-CHOW) was put on a regular chow diet (Altromin 1324, Brogaarden, Denmark) for 35 weeks prior to the study.

Figure 6:
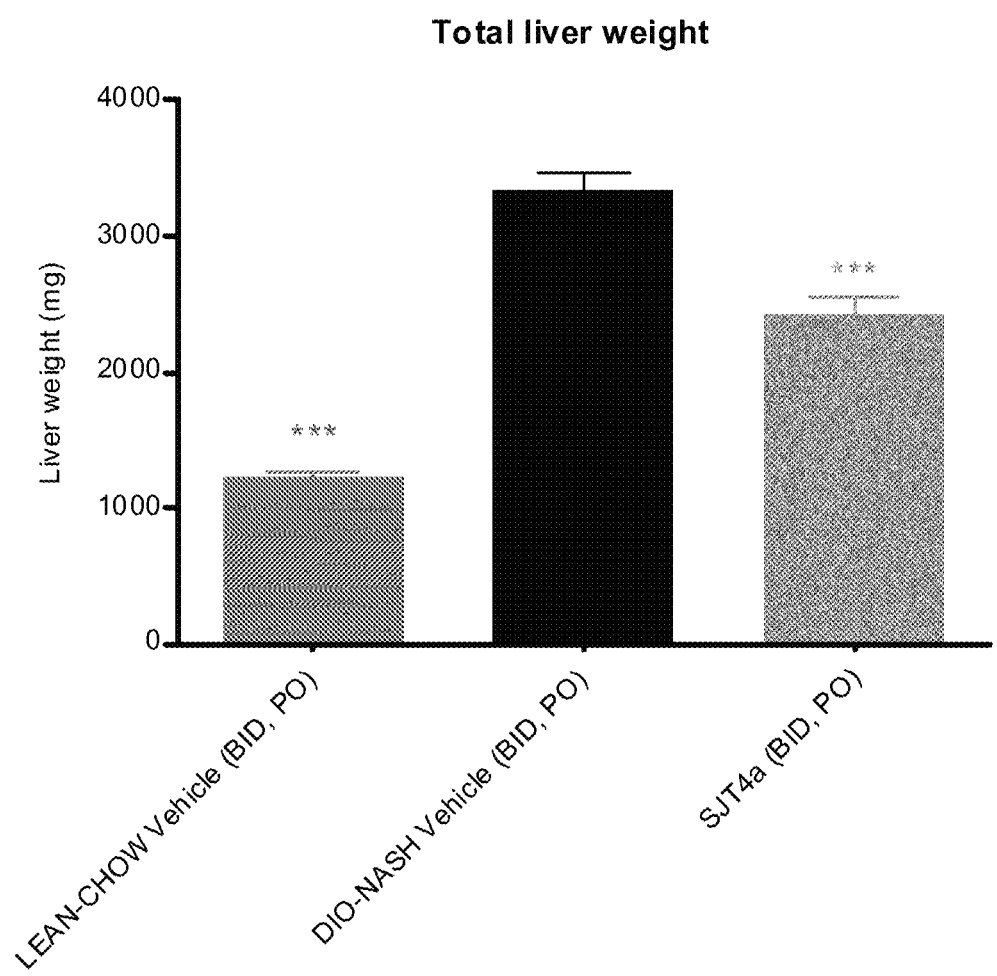
FIG. 6: shows the in vivo effect of a hydrochloride salt of compound 4a (SJT4a) in the total liver weight. DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl).

FIG. 6 shows the total liver weight at the end of the assay, wherein DIO-NASH mice control group treated with vehicle (central column) showed increased weight compared to the LEAN-CHOW mice control group also treated with vehicle (left column), whereas DIO-NASH mice group treated with a hydrochloride salt of compound 4a (right column) presented reduced liver weight compared to the DIO-NASH mice control group.

Data expressed as mean±s.e.m. values from 10-12 animals, *** p<0.001, vs DIO-NASH vehicle; One-way ANOVA with Dunnett's Multiple Comparison Test (all columns against DIO-NASH vehicle).

Example 4: In Vivo Effect of Compound 4a on Absolute and Relative Body Weight

The assay was carried out to evaluate the effect of the compounds of the invention on body weight of animals with non-alcoholic fat liver disease (DIO-NASH mice). For this assay, the effect of compound 4a in absolute and relative body weight was evaluated. DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl). The DIO-NASH mice group were put on high fat diet (40% AMLN diet, D09100301 Research Diets, USA) and a control group (LEAN-CHOW) was put on a regular chow diet (Altromin 1324, Brogaarden, Denmark) for 35 weeks prior to the study.

Body weight of for each of the groups taken on a daily basis. The animals were kept under the same conditions were used as in example 2.2.

Figure 7A:
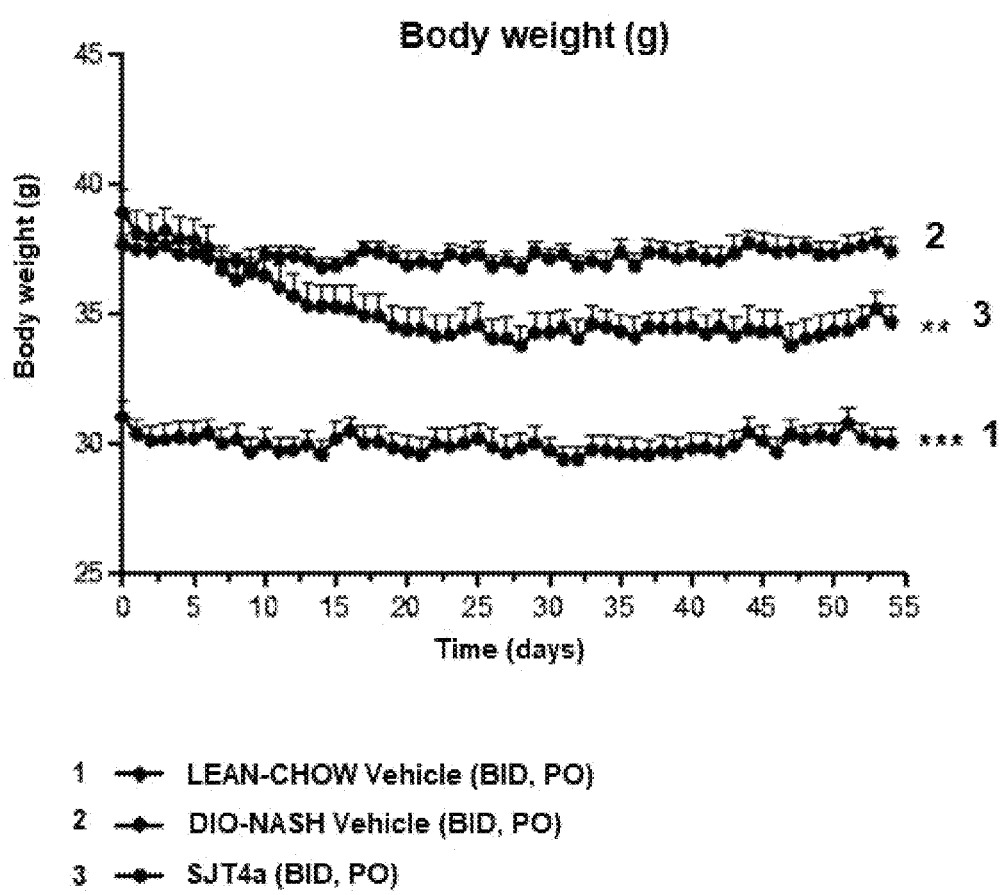
FIG. 7: A shows the in vivo effect of a hydrochloride salt of compound 4a (SJT4a) in the absolute body weight, and B in relative body weight. In both cases DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl).

FIG. 7A shows the absolute body weight measured for each of the three animal groups. DIO-NASH mice treated with vehicle demonstrated increased body weight compared to LEAN-CHOW mice treated with vehicle, whereas treatment with a hydrochloride salt of compound 4a reduced body weight in DIO-NASH mice when compared to DIO-NASH mice treated with vehicle.

Data expressed as mean±s.e.m. values from 10-12 animals. P<0.01, *P<0.001 vs. NASH vehicle. One-way ANOVA with Dunnett's Multiple Comparative Test (against NASH vehicle) performed at day 54 of treatment.

Figure 7B:
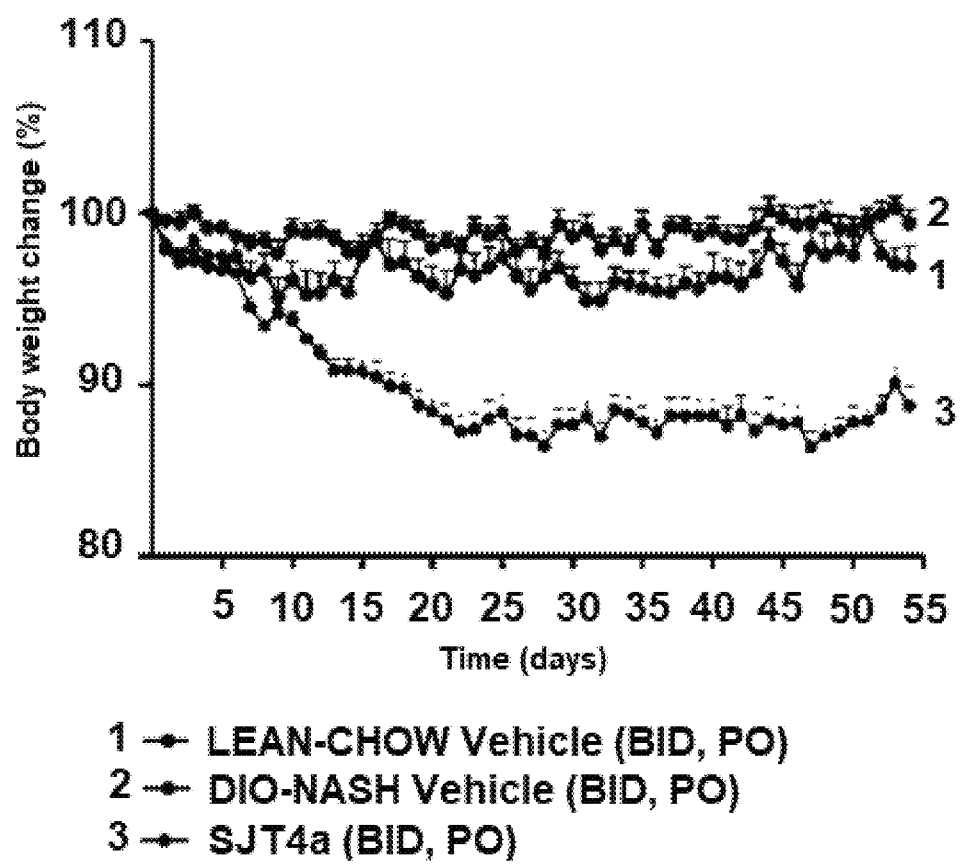

FIG. 7B shows the relative body weight measured for each of the three animal groups versus the body weight at the start of the treatment (day 0 is 100%). DIO-NASH and LEAN-CHOW animals treated with vehicle did not show significant weight changes during treatment with vehicle, whereas the treatment with a hydrochloride salt of compound 4a of DIO-NASH mice reduced relative body weight significantly.

Data expressed as mean±s.e.m. values from 10-12 animals. ***P<0.001 vs. NASH vehicle. One-way ANOVA with Dunnett's Multiple Comparative Test (against NASH vehicle) performed at day 54 of treatment.

Example 5: In Vivo Effect of Compound 4a on Liver Toxicity

The assay was carried out to evaluate the effect of the compounds of the invention on liver toxicity for animals with non-alcoholic fat liver disease (DIO-NASH mice). For this assay, the effect of compound 4a in plasma Alanine Aminotransferase (ALT) and in plasma Aspartate Aminotransferase (AST) was evaluated. DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl). The animals were kept under the same conditions were used as in example 2.2. The DIO-NASH mice group were put on high fat diet (40% AMLN diet, D09100301 Research Diets, USA) and a control group (LEAN-CHOW) was put on a regular chow diet (Altromin 1324, Brogaarden, Denmark) for 35 weeks prior to the study.

To evaluate Alanine transaminase (ALT) and Aspartate transaminase (AST), blood samples were collected in heparinized tubes and plasma was separated and stored at −80° C. until analysis. ALT and AST were measured using commercial kits (Roche Diagnostics, Germany) on the Cobas™ C-501 autoanalyzer according to the manufacturer's instructions.

Figure 8A:
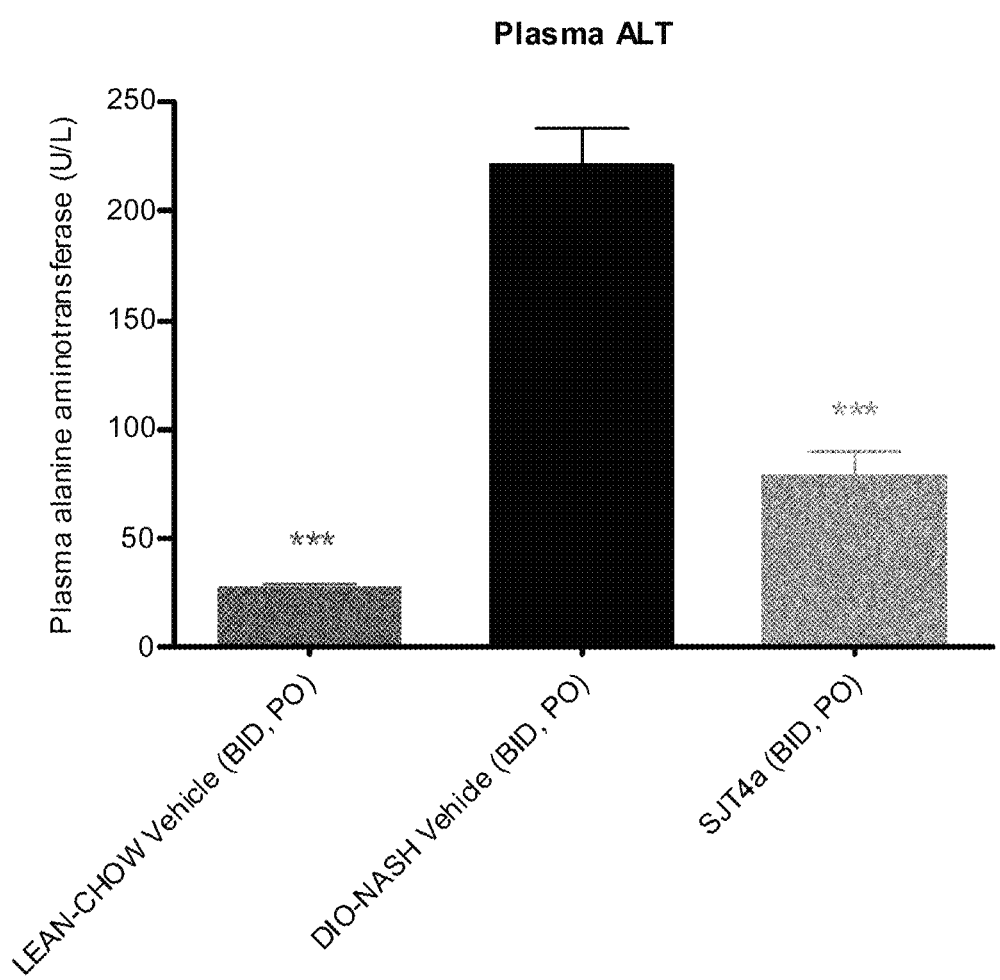
FIG. 8: A shows the in vivo effect of a hydrochloride salt of compound 4a (SJT4a) in plasma ALT (alanine aminotransferase). B shows the in vivo effect of a hydrochloride salt of compound 4a (SJT4a) in plasma AST (aspartate aminotransferase). In both cases DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl).

FIG. 8A shows the plasma ALT (U/L) for each of the three animal groups at the end of the treatment. DIO-NASH control group treated with vehicle showed increased plasma ALT compared to LEAN-CHOW animals. Treatment with a hydrochloride salt of compound 4a reduced the plasma ALT levels of DIO-NASH animals when compared to the DIO-NASH animals treated with vehicle.

Data expressed as mean±s.e.m. values from 10-12 animals. ***P<0.001 vs. NASH vehicle. One-way ANOVA with Dunnett's Multiple Comparative Test (all columns against NASH vehicle).

Figure 8B:
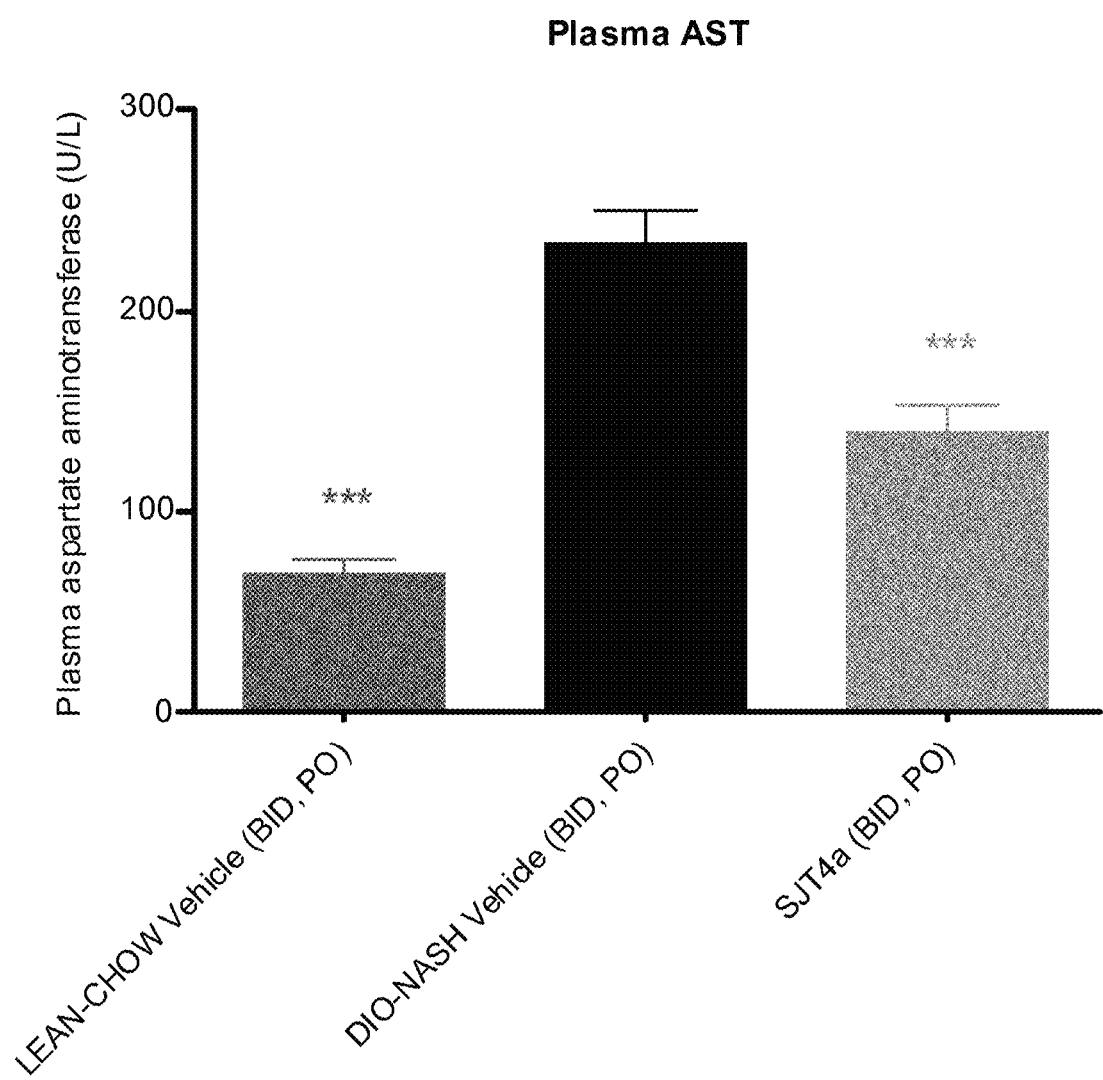

FIG. 8B shows the plasma AST (U/L) for each of the three animal groups at the end of the treatment. DIO-NASH control group treated with vehicle showed increased plasma AST compared to LEAN-CHOW animals. Treatment with a hydrochloride salt of compound 4a reduced the plasma AST levels of DIO-NASH animals when compared to the DIO-NASH animals treated with vehicle.

Data expressed as mean±s.e.m. values from 10-12 animals. ***P<0.001 vs. NASH vehicle. One-way ANOVA with Dunnett's Multiple Comparative Test (all columns against NASH vehicle).

Example 6: In Vivo Effect of Compound 4a on NAFLD Measured by NAFLD Activity Score (NAS), on Liver Fibrosis and on Liver Inflammation Non-alcoholic fat liver disease (NAFLD) activity score or NAS was evaluated by measurements of steatosis, lobular inflammation, ballooning degeneration and fibrosis of the liver.

Total NAS score represents the sum of scores for steatosis, inflammation, and ballooning, and ranges from 0-8 as follows:

| Feature | Degree | Score |
| --- | --- | --- |
| Steatosis | <5% | 0 |
| | 5-33% | 1 |
| | >33-66% | 2 |
| | >66% | 3 |
| Lobular inflammation | No foci | 0 |
| | <2 foci/200x | 1 |
| | 2-4 foci/200x | 2 |
| | >4 foci/200x | 3 |
| Ballooning degeneration | None | 0 |
| | Few | 1 |
| | Many cells/prominent ballooning | 2 |
| Fibrosis | None | 0 |
| | Perisinusoidal or periportal | 1 |
| | Perisinusoidal & portal/periportal | 2 |
| | Bridging fibrosis | 3 |
| | Cirrhosis | 4 |

The % of steatosis degree refers to the amount of surface area of the sample involved by steatosis as evaluated on low to medium power examination.

The value given to measure inflammation corresponds to the number of inflammatory foci per field using a 200× magnification. A focus is defined as a cluster, not a row, of >3 inflammatory cells. Acidophil bodies are not included in the inflammatory assessment.

The ballooning degeneration value is measured by the amount of balloon cells, corresponding to degenerated hepatocytes with cleared cytoplasm, enlargement, swelling, rounding and reticulated cytoplasm.

To assess the effect of compound 4a in NAS in mice with non-alcoholic fat liver disease, DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl). The animals were kept and examined under the same conditions were used as in example 2.2. The liver biopsies were also carried out under the same conditions as in example 2.2. The DIO-NASH mice group were put on high fat diet (40% AMLN diet, D09100301 Research Diets, USA) and a control group (LEAN-CHOW) was put on a regular chow diet (Altromin 1324, Brogaarden, Denmark) for 35 weeks prior to the study.

Liver samples were fixed in formalin, paraffin embedded, and sections were stained with hematoxylin and eosin (H&E) and Sirius Red. Samples are scored for NAS and fibrosis using of the clinical criteria outlined by Kleiner et al. 2005.

Figure 9:
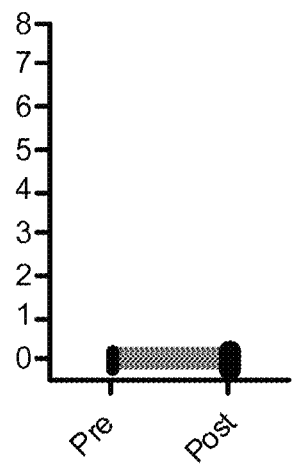
FIG. 9: In vivo assay to measure NAFLD activity score (NAS) in (A) LEAN-CHOW mice treated with vehicle, (B) DIO-NASH mice treated with vehicle or (C) with a hydrochloride salt of compound 4a (SJT4a) 50 mg/kg, p.o., b.i.d., during 8 weeks.
Figure 9:
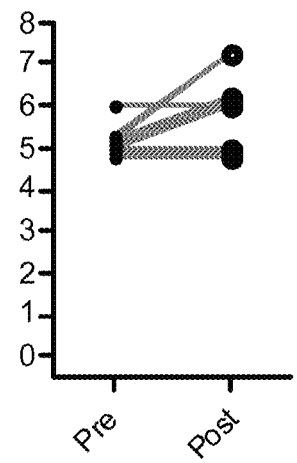
Figure 9:
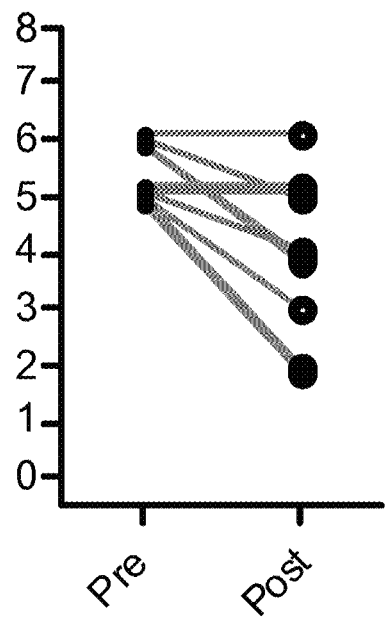

FIG. 9 shows the NAS score change of the liver biopsy pre and post study for each of the groups of animals. For each animal, the change from the pre-study biopsy to the post-study biopsy is indicated by a line.

FIG. 9A shows no significant changes in the LEAN-CHOW group NAS scores (control treated with vehicle), wherein all animals show low scores both before and after the study. FIG. 9B shows how DIO-NASH mice feature higher scores prior the study when compared to the scores of LEAN-CHOW mice, and how the scores tend to increase after the study. FIG. 9C shows how DIO-NASH mice treated with a hydrochloride salt of compound 4a generally reduced the NAS score after the treatment.

To assess the effect of the compounds of the invention in fibrosis of liver in the treatment of non-alcoholic fat liver disease, the collagen type I (a fibrosis marker) in liver was measured after the 8 weeks of the study where DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl).

Type I collagen content was measured by IHC staining: Type I collagen (Southern Biotech, Cat. 1310-01) IHC was performed using standard procedures. Briefly, after antigen retrieval and blocking of endogenous peroxidase activity, liver slides were incubated with primary antibody. The primary antibody was detected using biotinylated secondary antibody and amplified using a vectastain-TSA-vectastain method a polymeric HRP-linker antibody conjugate. Next, the primary antibody was visualized with DAB as chromogen. Finally, sections were counterstained in hematoxylin and cover-slipped.

Figure 10A:
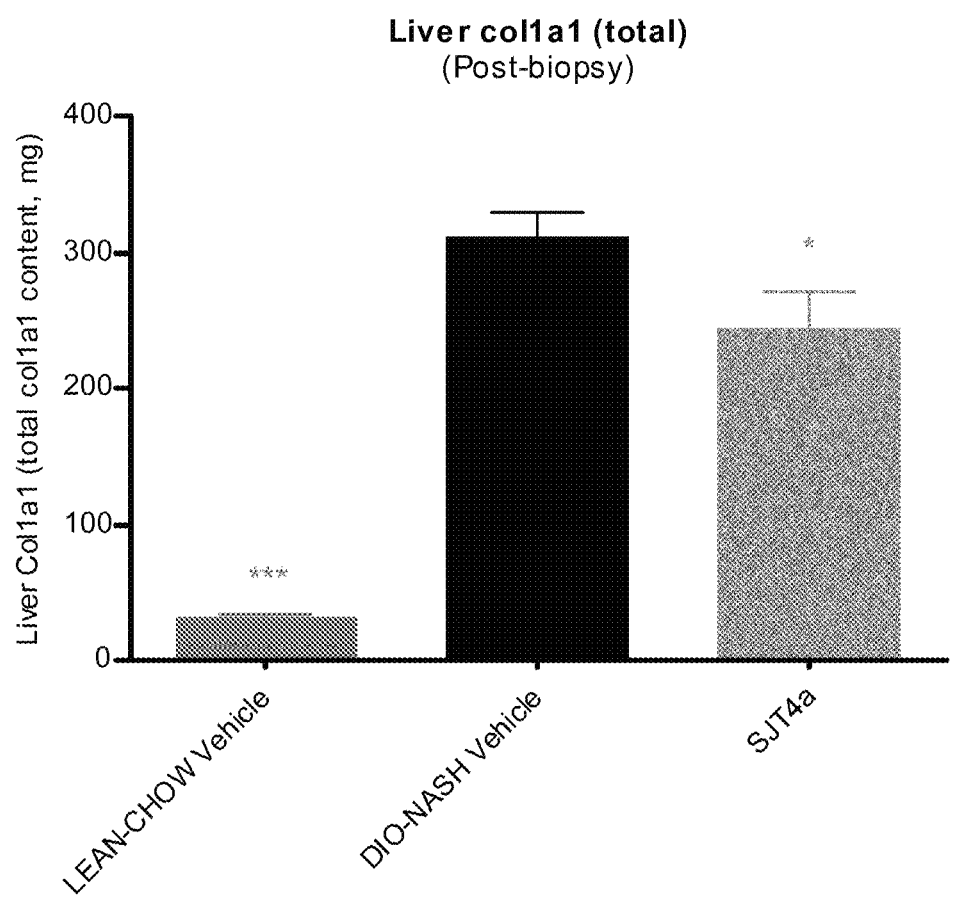
FIG. 10: A shows in vivo effect of a hydrochloride salt of compound 4a (SJT4a) in liver fibrosis, measuring collagen type I (col1a1) as a fibrosis marker. Liver samples were obtained from DIO-NASH mice (C57Bl/6J male mice) treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl). B shows representative images of liver samples for each of the previous mice groups stained with anti-type I collagen at the end of the study (magnification 20×).

FIG. 10A shows the quantification of the total content of liver collagen type 1 (col1a1) determined by morphometry in the three groups of mice. DIO-NASH control mice group treated with vehicle demonstrated increased liver col1a1 compared to the LEAN-CHOW control group also treated with vehicle. DIO-NASH mice treated with a hydrochloride salt of compound 4a showed reduced total liver col1a1 compared to the DIO-NASH control group treated with vehicle.

Data expressed as mean±s.e.m. values from 10-12 animals. *P<0.05, ***P<0.001 vs. NASH vehicle. One-way ANOVA with Dunnett's Multiple Comparative Test (all columns against NASH vehicle).

Figure 10B:
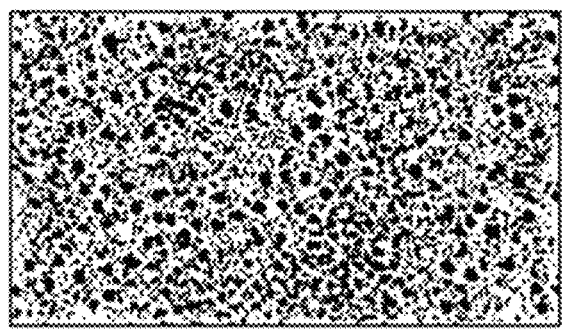
Figure 10B:
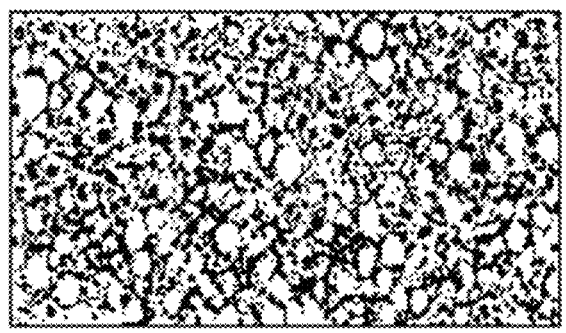
Figure 10B:
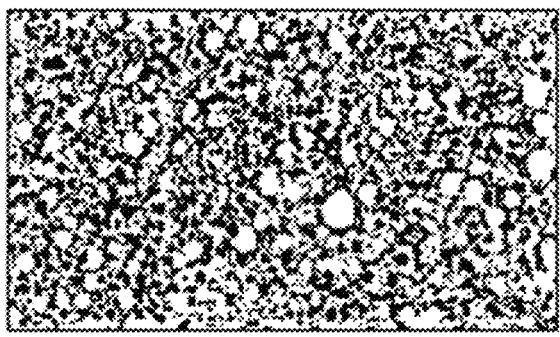

FIG. 10B shows representative images of liver samples for each of the mice groups stained with anti-type I collagen (col1a1) at the end of the study (magnification 20×). The images show a visible change in this fibrosis marker after DIO-NASH animals were treated with a hydrochloride salt of compound 4a, confirming the results of FIG. 10A.

To assess the effect of the compounds of the invention in inflammation of liver in the treatment of non-alcoholic fat liver disease, liver galactin-3 (inflammation marker) levels were determined after a 8 weeks study where DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl).

Galectin-3 was measured via galtactin-3 IHC staining: galectin-3 (Biolegend, Cat. #125402) IHC were performed using standard procedures. Briefly, after antigen retrieval and blocking of endogenous peroxidase activity, slides were incubated with primary antibody. The primary antibody was detected using a linker secondary antibody followed by amplification using a polymeric HRP-linker antibody conjugate. Next, the primary antibody was visualized with DAB as chromogen. Finally, sections were counterstained in hematoxylin and cover-slipped.

Figure 11A:
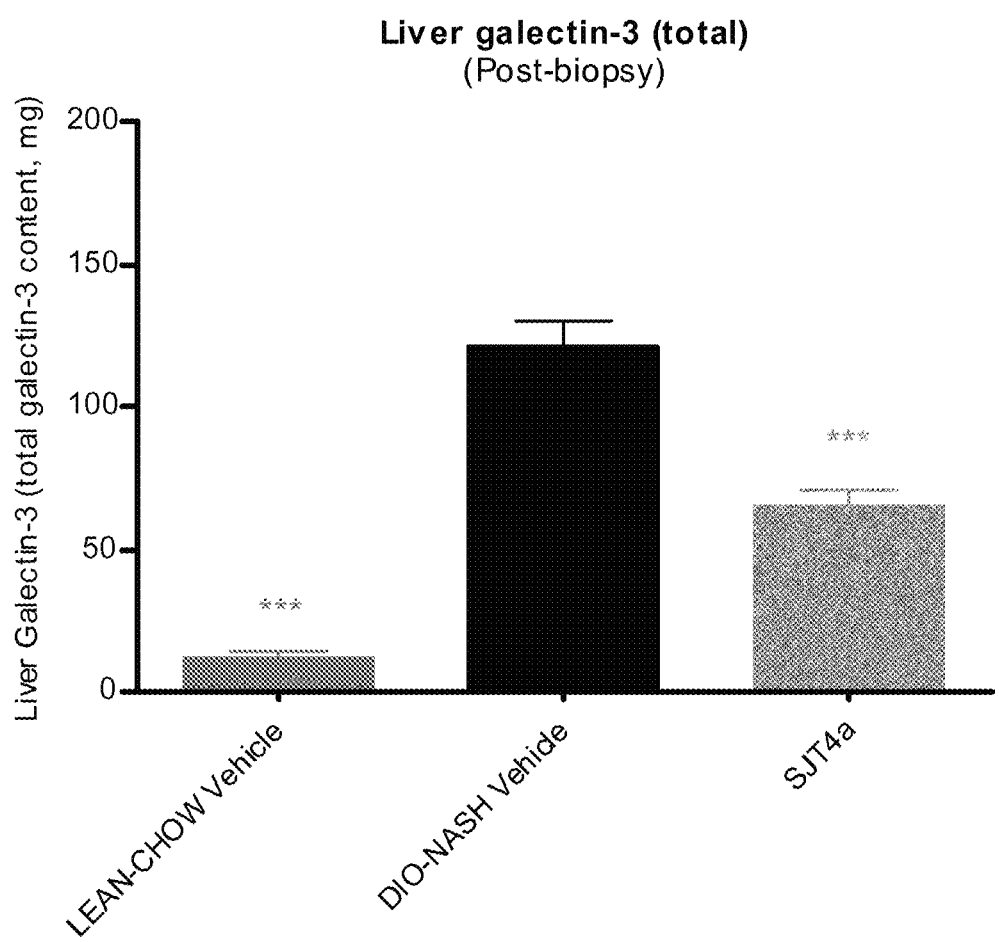
FIG. 11: A shows in vivo effect of a hydrochloride salt of compound 4a (SJT4a) in liver inflammation, measuring galectin-3 as an inflammation marker. Liver samples were obtained from DIO-NASH mice (C57Bl/6J male mice) treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl). B shows representative images of liver samples for each of the mice groups stained with anti-galectin-3 at the end of the study (magnification 20×).

FIG. 11A shows the quantification of the total liver galectin-3 content determined by morphometry in the three groups of mice. DIO-NASH control mice group treated with vehicle demonstrated increased galectin-3 content compared to the LEAN-CHOW control group also treated with vehicle. DIO-NASH mice treated with a hydrochloride salt of compound 4a showed reduced total galectin-3 content compared to the DIO-NASH control group treated with vehicle.

Data expressed as mean±s.e.m. values from 10-12 animals. ***P<0.001 vs. NASH vehicle. One-way ANOVA with Dunnett's Multiple Comparative Test (all columns against NASH vehicle).

Figure 11B:
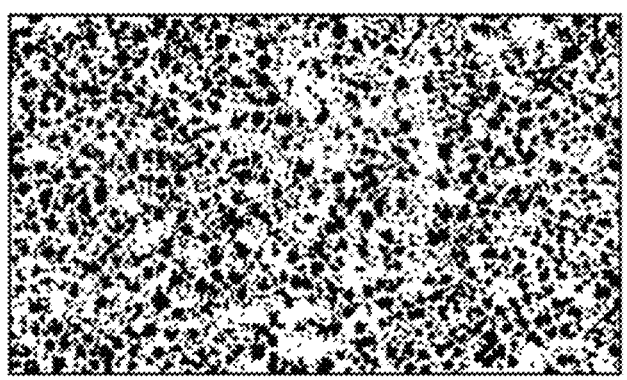
Figure 11B:
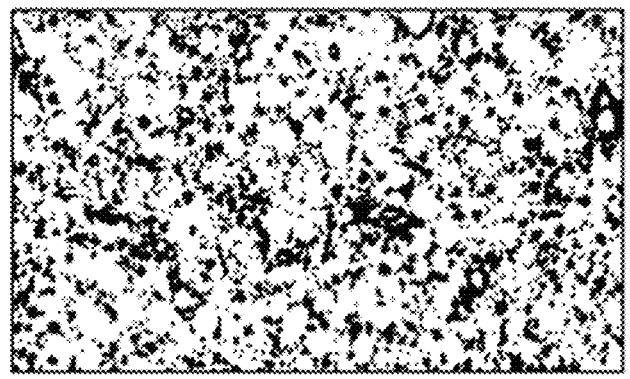
Figure 11B:
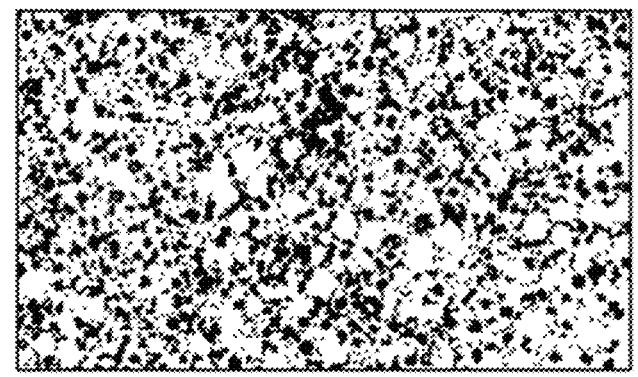

FIG. 11B shows representative images of liver samples for each of the mice groups stained with anti-galectin-3 at the end of the study (magnification 20×). The images show a visible change in this inflammation marker after DIO-NASH animals were treated with a hydrochloride salt of compound 4a, confirming the results of FIG. 11A.

Example 7: Differential Expression Analysis: In Vivo Effect of Compound 4a

The effect of the compounds of the invention in the development of liver fibrosis was also studied by differential gene expression analysis by RNAseq where DIO-NASH mice (C57Bl/6J male mice) were treated with a hydrochloride salt of compound 4a during 8 weeks (50 mg/kg, p.o., b.i.d.), versus a pathological control of DIO-NASH mice and a non-pathological control LEAN-CHOW mice, both treated with the vehicle (0.9% NaCl).

The animals were kept and examined under the same conditions were used as in example 2.2. The liver biopsies were also carried out under the same conditions as in example 2.2. The DIO-NASH mice group were put on high fat diet (40% AMLN diet, D09100301 Research Diets, USA) and a control group (LEAN-CHOW) was put on a regular chow diet (Altromin 1324, Brogaarden, Denmark) for 35 weeks prior to the study.

Figure 12:
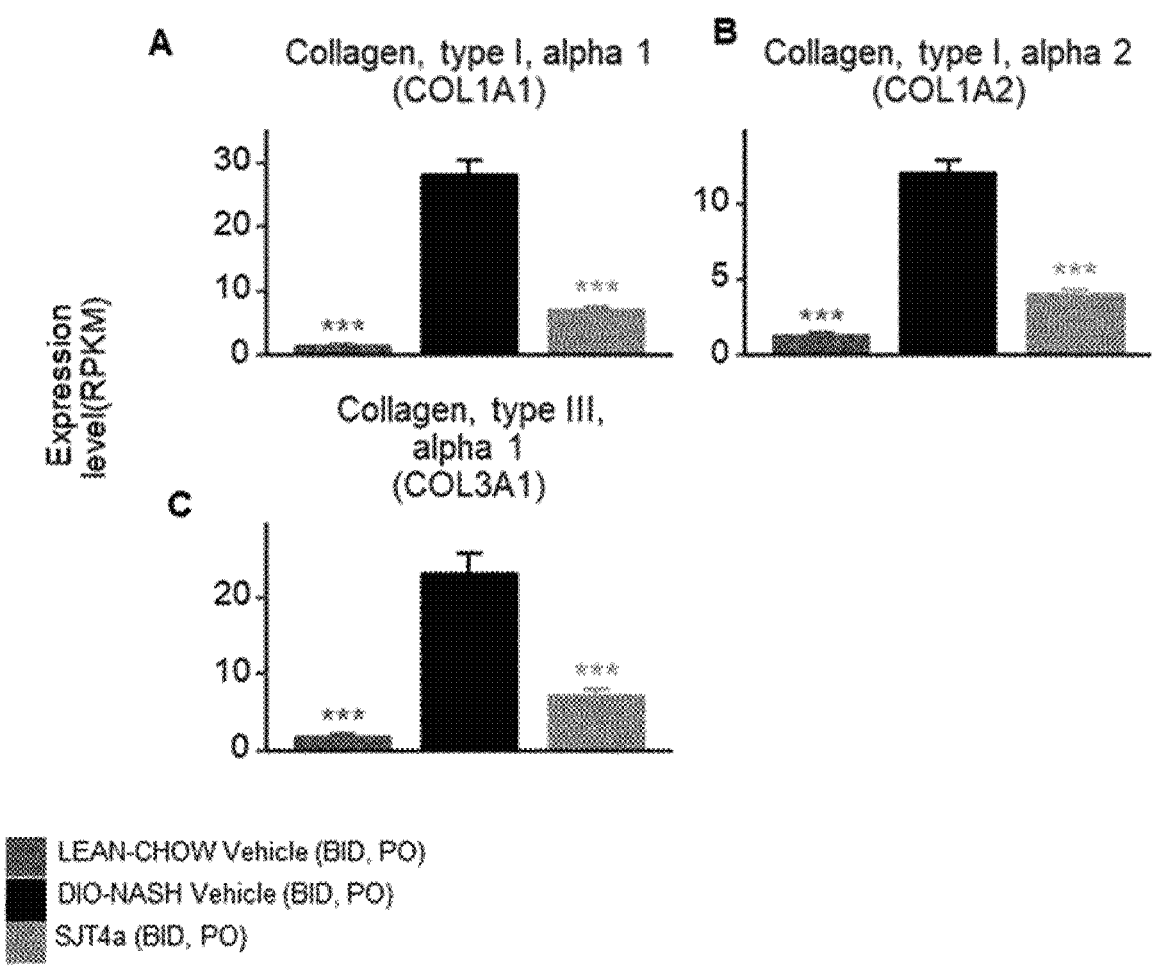
FIG. 12: effect of 8 weeks treatment of DIO-NASH mice with a hydrochloride salt of compound 4a (SJT4A) 50 mg/kg, p.o., b.i.d., versus a pathological control of DIO-NASH mice and a non-pathological control LEAN-CHOW mice, both treated with the vehicle (0.9% NaCl), in the expression of collagen genes as fibrosis markers: (A) collagen type 1-alpha 1 (COL1A1) and (B) alpha 2 (COL1A2) and (C) collagen type III alpha 1 (COL3A1).
Figure 13:
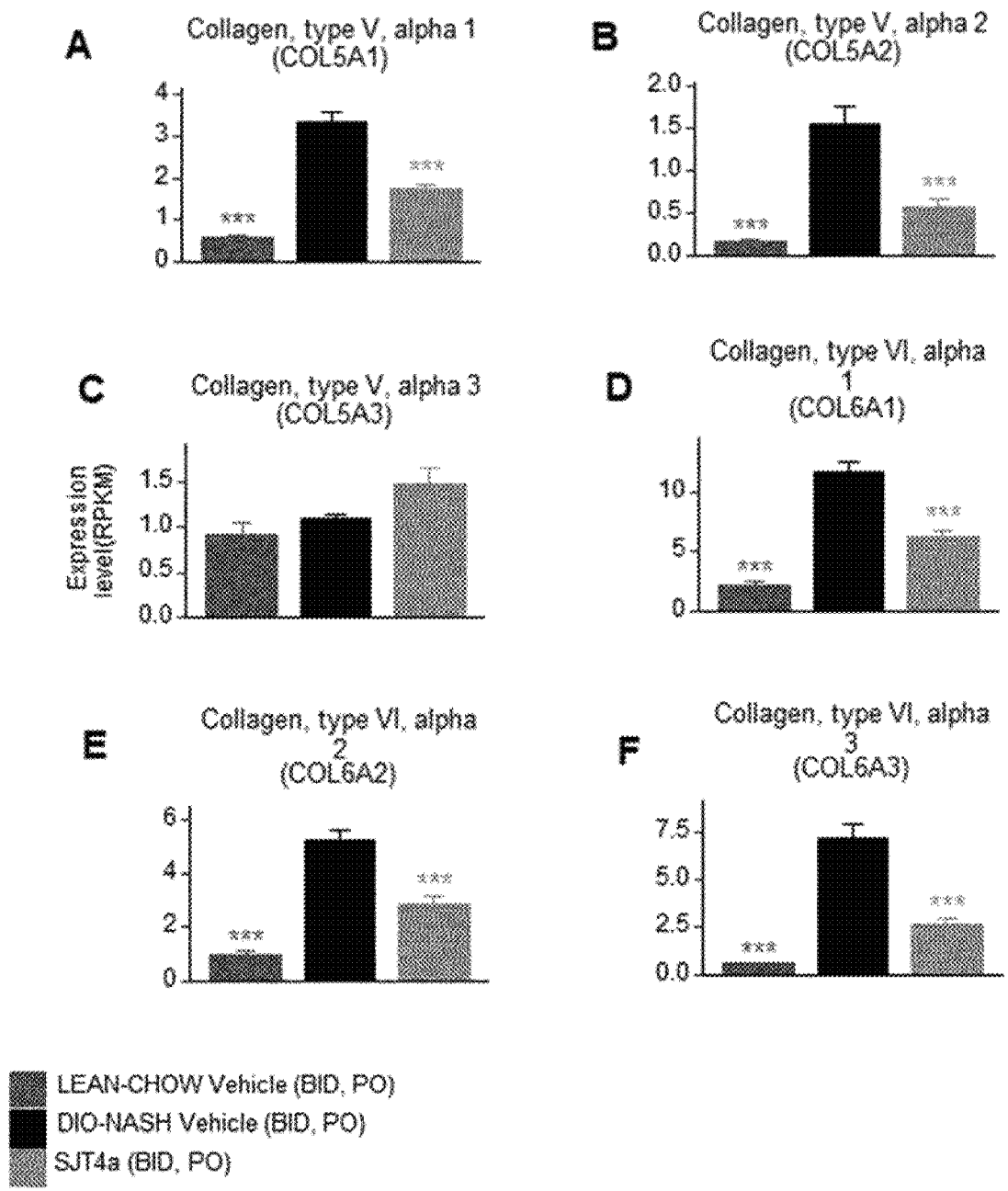
FIG. 13: effect of 8 weeks treatment of DIO-NASH mice with a hydrochloride salt of compound 4a (SJT4a) 50 mg/kg, p.o., b.i.d., versus a pathological control of DIO-NASH mice and a non-pathological control LEAN-CHOW mice, both treated with the vehicle (0.9% NaCl), in the expression of collagen genes as fibrosis markers: (A) collagen V alpha 1 (COL5A1), (B) alpha 2 (COL5A2) and (C) alpha 3 (COL5A3), (13) collagen type VI alpha 1 (COL6A1), (E) alpha 2 (COL6A2) and (F) alpha 3 (COL6A3).

FIGS. 12 and 13 show the effect of treatment of DIO-NASH mice with a hydrochloride salt of compound 4a versus a control DIO-NASH mice group treated with vehicle and a LEAN-CHOW positive control group also treated with vehicle, in the expression of collagen genes which are fibrosis markers: collagen type I-alpha 1 (COL1A1) and alpha 2 (COL1A2), collagen type III alpha 1 (COL3A1), collagen V alpha 1 (COL5A1), alpha 2 (COL5A2) and alpha 3 (COL5A3), collagen type VI alpha 1 (COL6A1), alpha 2 (COL6A2) and alpha 3 (COL6A3).

Results are given as expression level in RPKM for each mice group, wherein RPKM (Reads per kilo base per million mapped reads) is a method of quantifying gene expression from RNA sequencing data by normalizing for total read length and the number of sequencing reads.

Date expressed as mean±s.e.m. values from 6 animals. ***P<0.001 vs. NASH vehicle.

The treatment of DIO-NASH model mice with a hydrochloride salt of compound 4a significantly reduced the expression of the collagen genes compared to the control DIO-NASH mice group. In fact, compound 4a induced regulation of more than 2000 genes, where many are associated with NASH. In particular, treatment with compound 4a of DIO-NASH mice (50 mg p.o., b.i.d) during 8 weeks:

produced reduction in several prototypical inflammation markers related to monocyte recruitment, such as CD68, CCR2, MAC-2;

produced reduction in several prototypical fibrosis genes related to stellate cell activation, such as Col1a1, Col3a1 and TIMP1;

in relation to inflammation signaling produced a reduction in TLR4, TGFB and TGFBR gene expression in relation to insulin signaling produced a decreased expression of MAPK and AKT and an increased expression of GLUT4;

in relation to lipid metabolism produced a decreased expression of CD36 and an increased expression of SQLE; and in relation to hepatocellular cell death produced an increased expression of Casp7 and IL18.

REFERENCES

1. Petta S, Muratore C, Craxi A. Non-alcoholic fatty liver disease pathogenesis: the present and the future. *Dig Liver Dis.* 2009; 41(9):615-25.
2. Neuschwander-Tetri B A. Non-alcoholic fatty liver disease. *BMC Med.* 2017; 15(1):45.
3. Bellentani S. The epidemiology of non-alcoholic fatty liver disease. *Liver Int.* 2017; 37 Suppl 1:81-84.
4. Hameed B, Terrault N. Emerging Therapies for Nonalcoholic Fatty Liver Disease. *Clin Liver Dis.* 2016; 20(2): 365-85.
5. Bashiardes S, Shapiro H, Rozin S, Shibolet O, Elinav E. Non-alcoholic fatty liver and the gut microbiota. *Mol Metab.* 2016; 5(9):782-94.
6. Barb D, Portillo-Sanchez P, Cusi K. Pharmacological management of nonalcoholic fatty liver disease. *Metabolism* 2016; 65(8):1183-95.
7. Ratziu V. Novel Pharmacotherapy Options for NASH. *Dig Dis Sci.* 2016; 61(5):1398-405.
8. Rotman Y, Sanyal A J. Current and upcoming pharmacotherapy for non-alcoholic fatty liver disease. *Gut* 2017; 66(1):180-190.

The invention claimed is:

1. A method for the treatment of non-alcoholic fat liver disease (NAFLD) and non-alcoholic steatohepatitis (NASH), and/or related symptoms and/or associated pathologies thereof comprising administering to a subject a compound of formula III, or pharmaceutically acceptable salt thereof:

Formula III

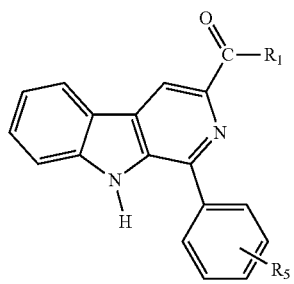

wherein, independently,

R$_1$ is selected from the group consisting of NH—(CH$_2$)$_n$—NH$_2$, NH—(CH$_2$)$_n$—N(CH$_3$)$_2$, NHCH$_2$CH$_2$OH; NHCH$_2$CH$_2$OCH$_3$, NH—N=CH-phenyl-R$_7$, and a cycled amine selected from:

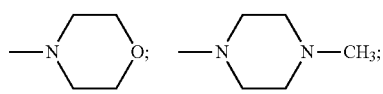

wherein n is an integer from 0 to 4;

R$_5$ is p-OCH$_3$; and

R$_7$ is H.

2. The method according to claim 1, wherein R$_1$ is selected from NH—(CH$_2$)$_n$—NH$_2$, NH—(CH$_2$)$_n$—N(CH$_3$)$_2$ or NH—N=CH-phenyl-R$_7$, wherein n is 2 or 3.

3. The method according to claim 1, wherein the pharmaceutically acceptable salt is a hydrochloride salt.

4. The method according to claim 1, wherein said compound is independently selected from 4a, 5a, 7a, 23a, 23b, 23c, 23d, 23e, 23f, 26a, 22a, 22b, 22c, 22d, 22e, or 22f:

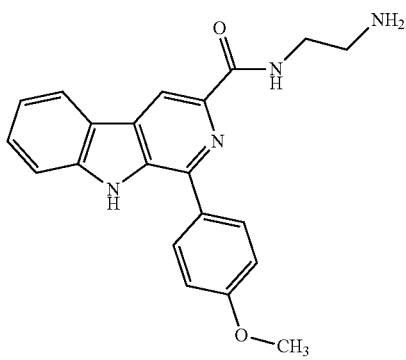
4a

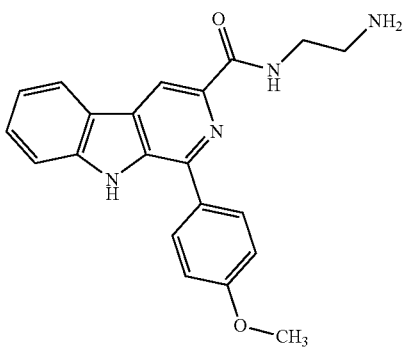
5a

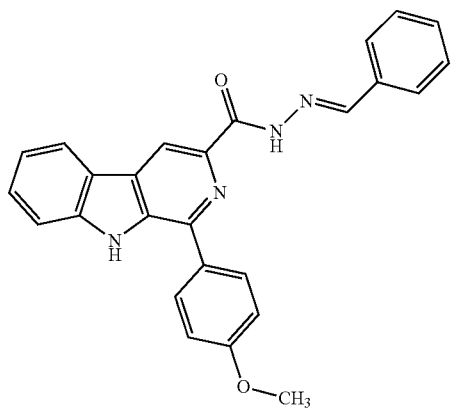
7a

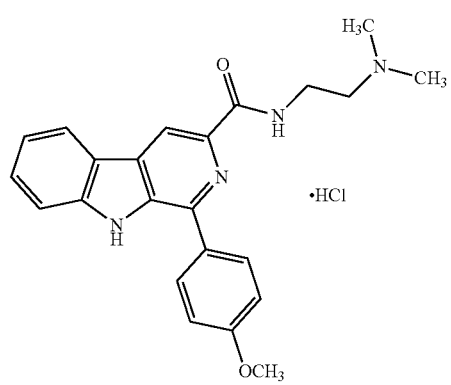
23b

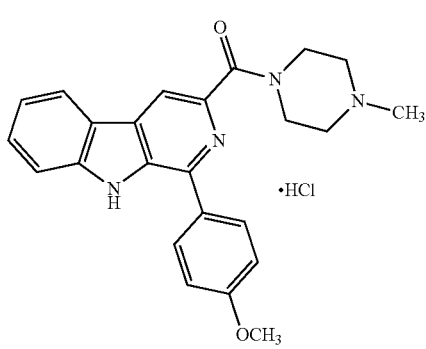
23c

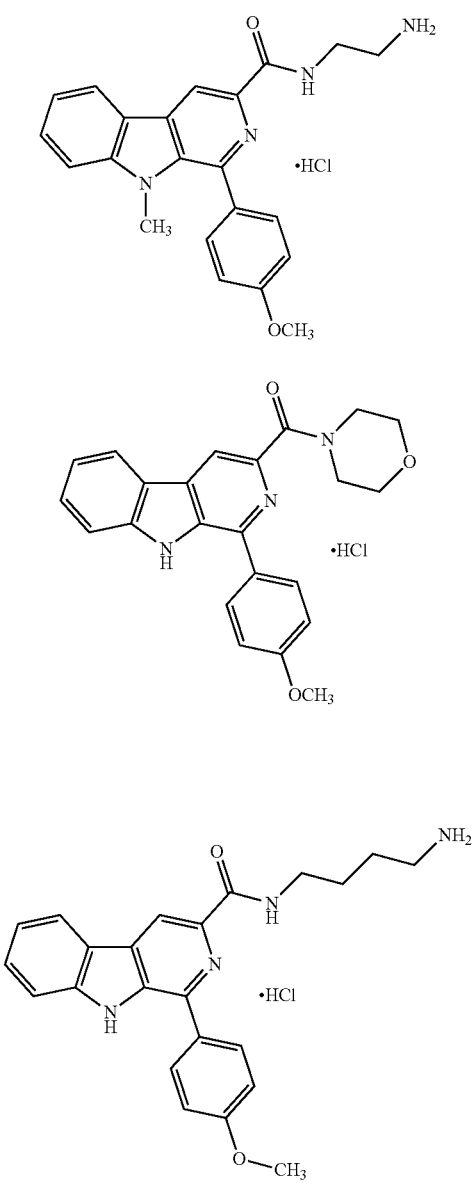
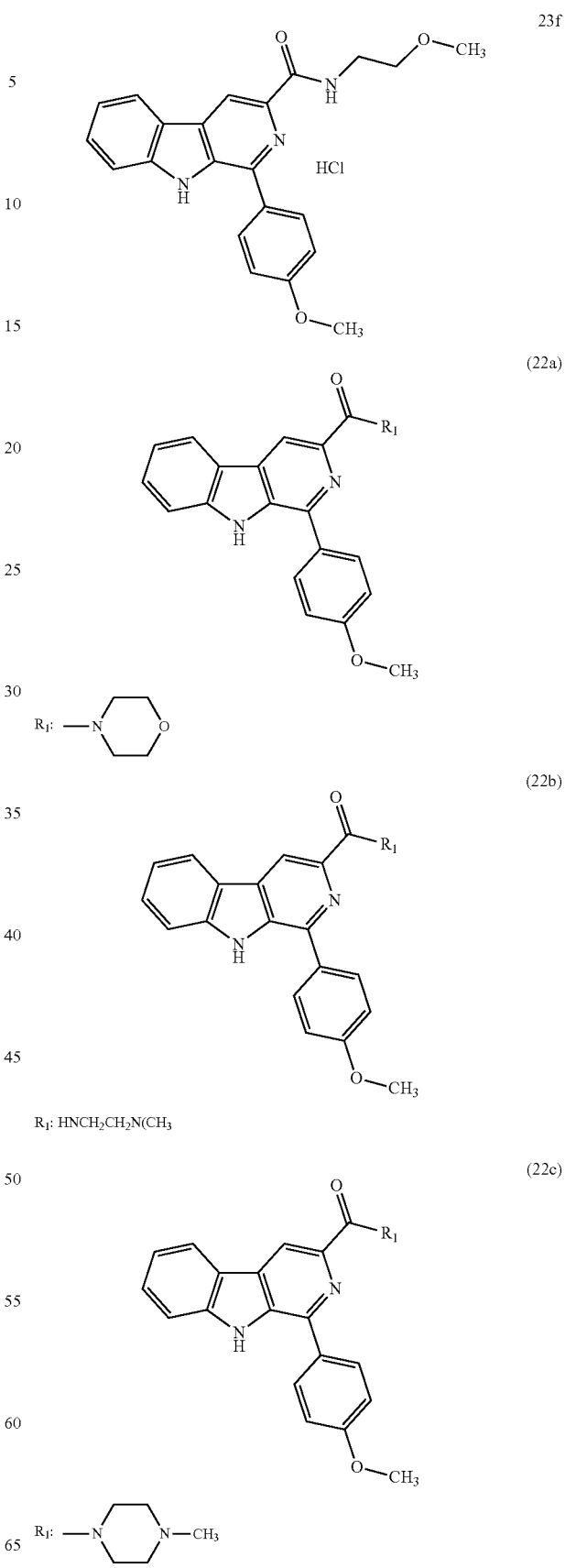

(22d)

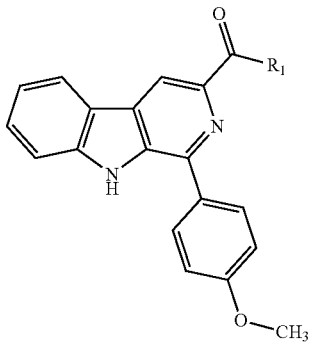

R₁: HNCH₂CH₂OH (22e)

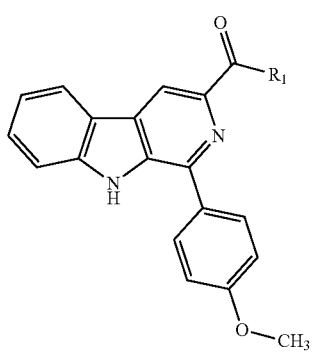

R₁: HN—(CH₂)₄—NH₂   or (22f)

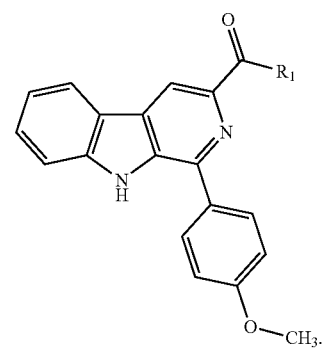

R₁: HNCH₂CH₂OCH₃

5. The method according to claim 1, wherein said compound is independently selected from 4a, 5a or 7a.

6. The method according to claim 1, wherein the related symptoms are independently selected from insulin resistance, lipid accumulation in the hepatocytes, mitochondrial dysfunction, oxidative stress, apoptosis, necrosis, inflammation or fibrosis.

7. The method according to claim 1, wherein the associated pathologies are cirrhosis or hepatocellular carcinoma.

8. A method for the treatment of non-alcoholic fat liver disease (NAFLD) and non-alcoholic steatohepatitis (NASH), and/or related symptoms and/or associated pathologies thereof, comprising administering to a subject in need thereof a pharmaceutical composition comprising at least one pharmaceutically acceptable excipient and an effective amount of at least one compound of formula III, or pharmaceutically acceptable salt thereof:

Formula III

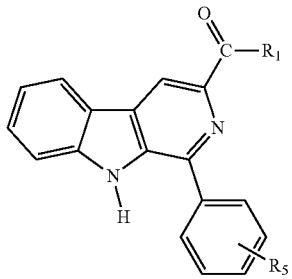

wherein, independently,

R₁ is selected from the group consisting of NH—(CH₂)ₙ—NH₂, NH—(CH₂)ₙ—N(CH₃)₂, NHCH₂CH₂OH, NHCH₂CH₂OCH₃, NH—N=CH-phenyl-R₇, and a cycled amine selected from:

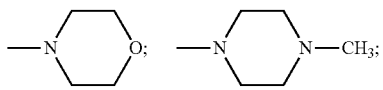

wherein n is an integer from 0 to 4;

R₅ is p-OCH₃; and

R₇ is H.

9. The method according to claim 8, wherein the pharmaceutical composition further comprises a second active compound independently selected from insulin sensitizers, bile acid regulators, inhibitors of de novo lipogenesis, lipid-lowering agents, antioxidants, anti-inflammatory agents, immune modulators, anti-apoptotic agents, gut microbiome modulators, or antifibrotics.

10. The method according to claim 8, wherein the related symptoms are independently selected from insulin resistance, lipid accumulation in the hepatocytes, mitochondrial dysfunction, oxidative stress, apoptosis, necrosis, inflammation or fibrosis.

11. The method according to claim 8, wherein the associated pathologies are cirrhosis or hepatocellular carcinoma.

12. The method according to claim 8, wherein

R₁ is selected from NH—(CH₂)ₙ—NH₂, NH—(CH₂)ₙ—N(CH₃)₂, or NH—N=CH-phenyl-R₇, wherein n is 2 or 3.

13. The method according to claim 8, wherein the pharmaceutically acceptable salt is a hydrochloride salt.

14. The method according to claim 8, wherein the at least one compound of formula I is independently selected from 4a, 5a, 7a, 23a, 23b, 23c, 23d, 23e, 23f, 26a, 22a, 22b, 22c, 22d, 22e, or 22f:

4a
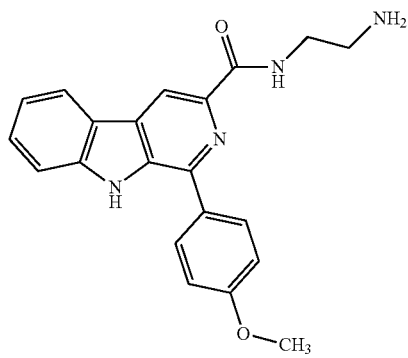
5a
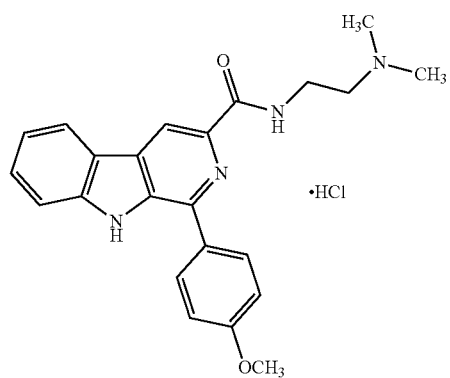
7a
23b
23c
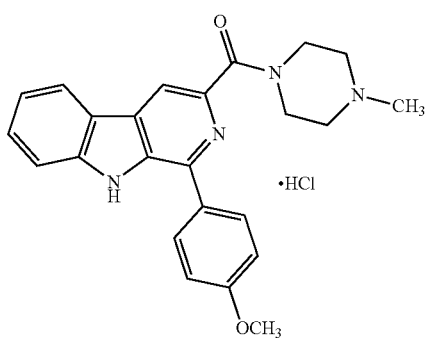
26a
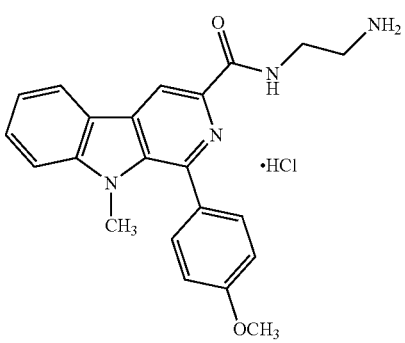
23a
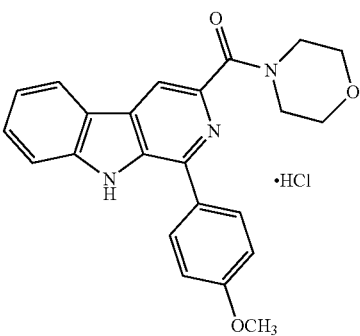
23e
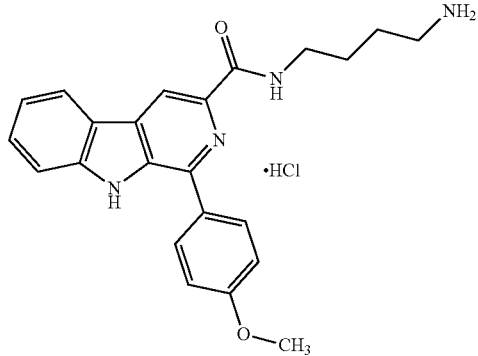

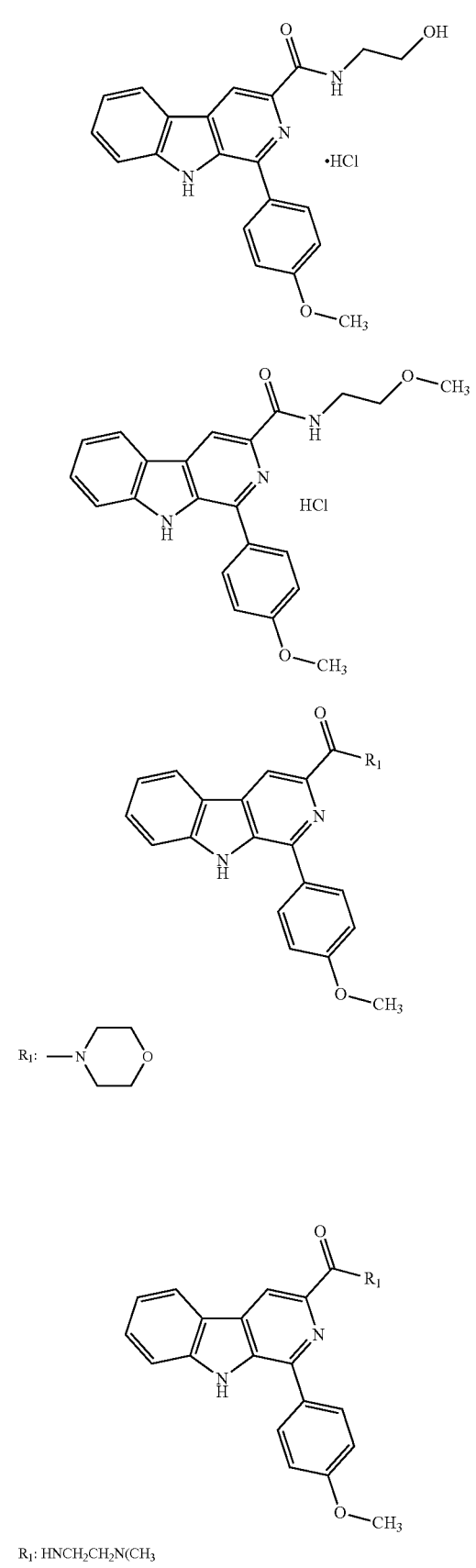
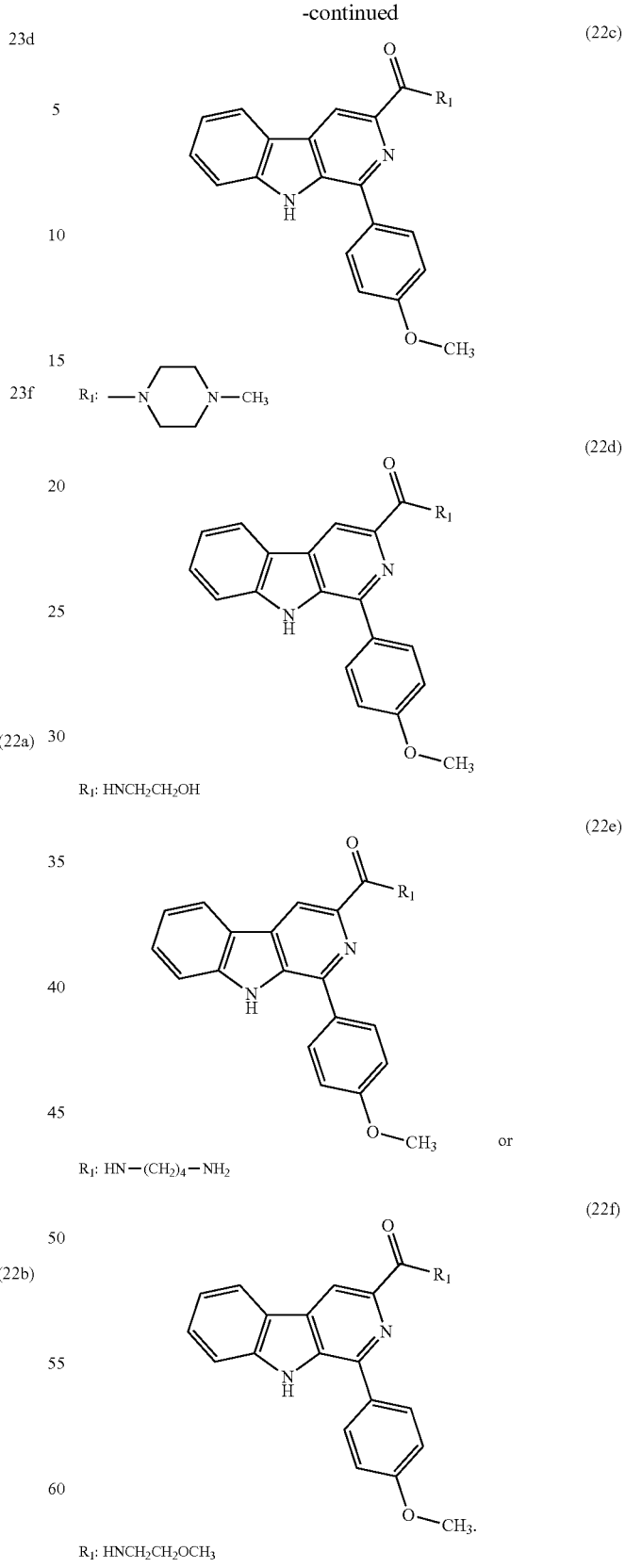
15. A method for alleviating non-alcoholic fat liver disease (NAFLD), non-alcoholic steatohepatitis (NASH), and/ or related symptoms and/or related pathologies thereof, comprising administering to a subject a nutraceutical composition comprising at least one food grade acceptable excipient and at least one compound of formula III, or food grade acceptable salt thereof:

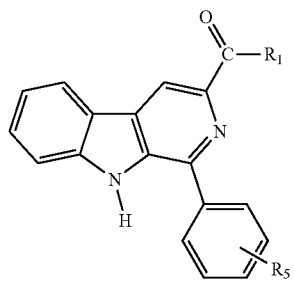

Formula III wherein, independently, $R_1$ is selected from the group consisting of NH—$(CH_2)_n$—$NH_2$, NH—$(CH_2)_n$—$N(CH_3)_2$, $NHCH_2CH_2OH$; $NHCH_2CH_2OCH_3$, NH—N=CH-phenyl-$R_7$, and a cycled amine selected from:

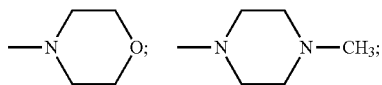

wherein n is an integer from 0 to 4;

$R_5$ is p-$OCH_3$; and $R_7$ is H.

16. The method according to claim 8, wherein the at least one compound of formula III is independently selected from 4a, 5a, or 7a.

17. The method according to claim 15, wherein $R_1$ is selected from NH—$(CH_2)_n$—$NH_2$, NH—$(CH_2)_n$—$N(CH_3)_2$, or NH—N=CH-phenyl-$R_7$, wherein n is 2 or 3.

18. The method according to claim 15, wherein the at least one compound of formula I is independently selected from 4a, 5a, 7a, 23a, 23b, 23c, 23d, 23e, 23f, 26a, 22a, 22b, 22c, 22d, 22e, or 22f:

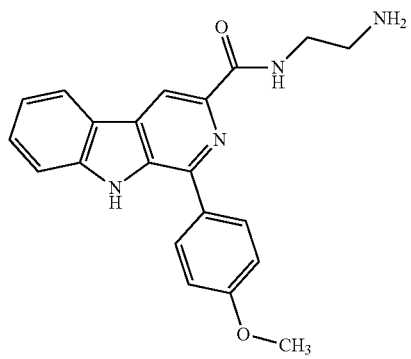

4a

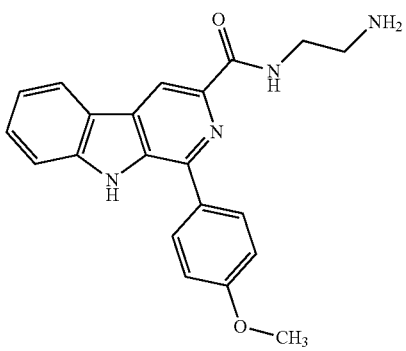

5a

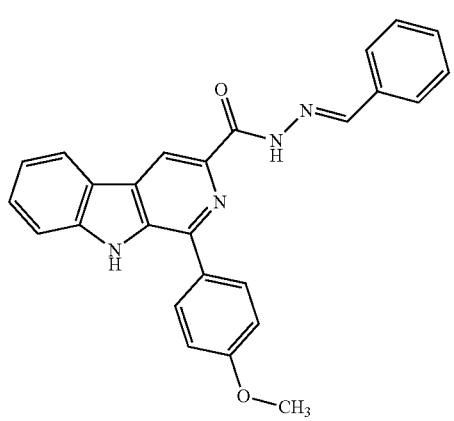

7a

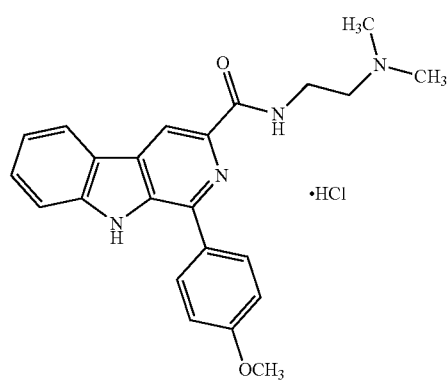

23b

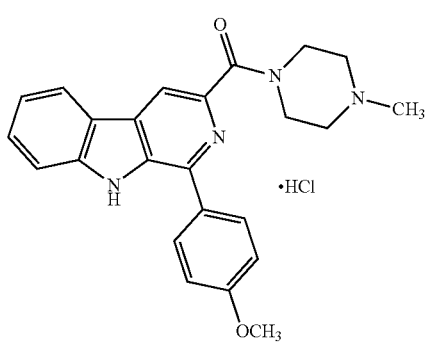

23c

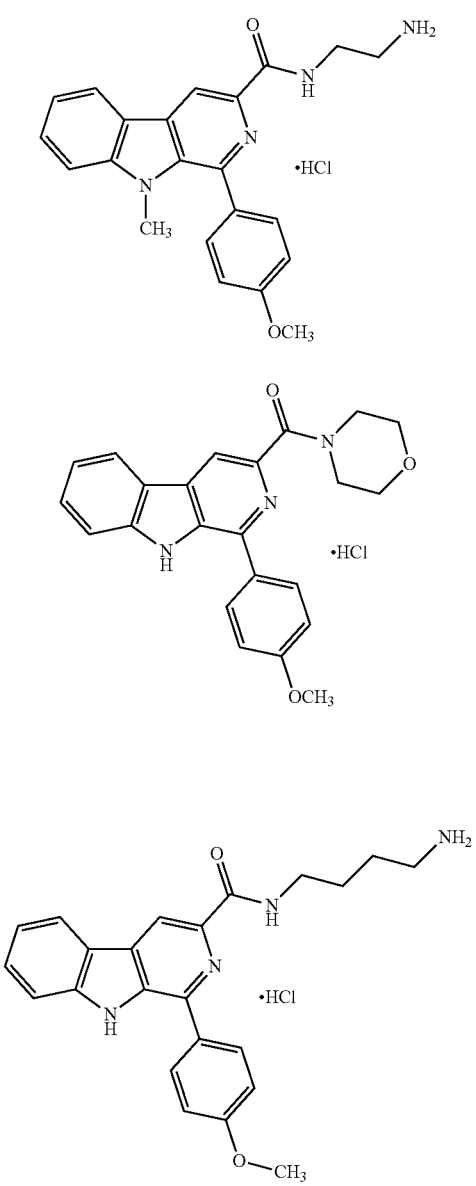
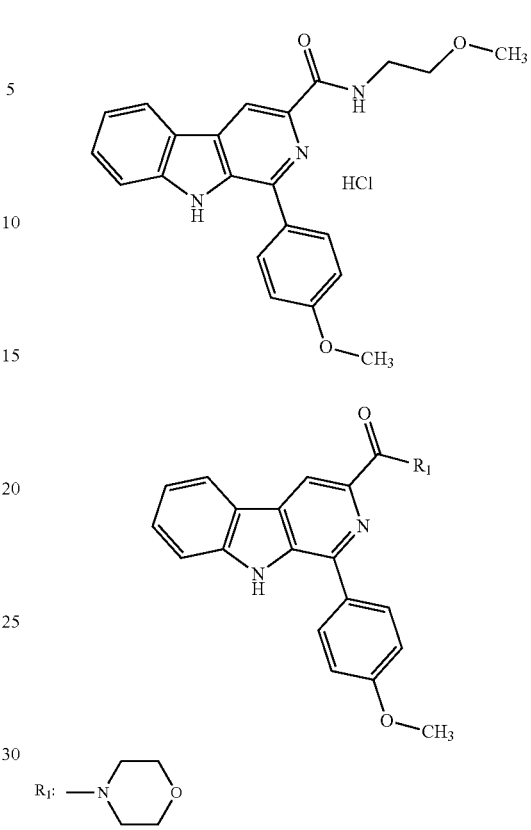
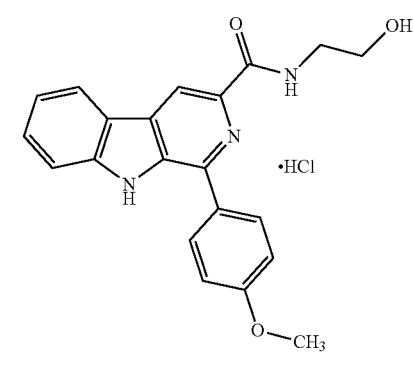

(22d)
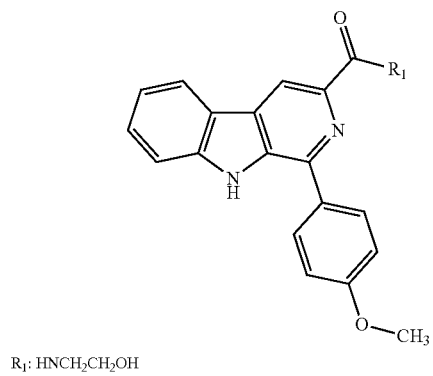
R₁: HNCH₂CH₂OH
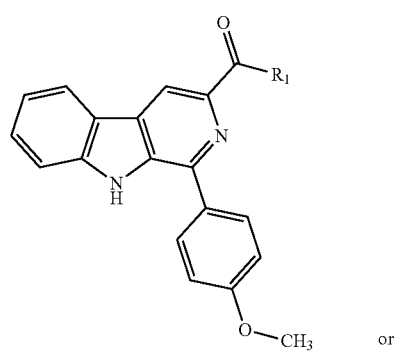
or
(22e)
R₁: HN—(CH₂)₄—NH₂
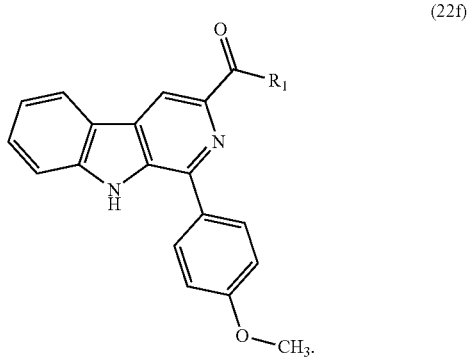
R₁: HNCH₂CH₂OCH₃
19. The method according to claim 15, wherein the at least one compound of formula III is independently selected from 4a, 5a, or 7a.
* * * * *